(12) United States Patent
Zabinski et al.

(10) Patent No.: US 11,969,250 B2
(45) Date of Patent: Apr. 30, 2024

(54) SCALABLE MULTI-RESOLUTION ELECTRODE ARRAY FOR SENSING AND STIMULATING THE BRAIN

(71) Applicant: Mayo Foundation for Medical Education and Research, Rochester, MN (US)

(72) Inventors: Patrick J. Zabinski, Stewartville, MN (US); Gregory A. Worrell, Rochester, MN (US); Clifton R. Haider, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 103 days.

(21) Appl. No.: 17/765,165

(22) PCT Filed: Nov. 13, 2020

(86) PCT No.: PCT/US2020/060408
§ 371 (c)(1),
(2) Date: Mar. 30, 2022

(87) PCT Pub. No.: WO2021/097202
PCT Pub. Date: Feb. 20, 2021

(65) Prior Publication Data
US 2022/0369985 A1 Nov. 24, 2022

Related U.S. Application Data

(60) Provisional application No. 62/935,400, filed on Nov. 14, 2019.

(51) Int. Cl.
*H03M 1/12* (2006.01)
*A61B 5/291* (2021.01)
*A61B 5/304* (2021.01)

(52) U.S. Cl.
CPC .............. *A61B 5/291* (2021.01); *A61B 5/304* (2021.01)

(58) Field of Classification Search
CPC .......... A61B 5/291; A61B 5/304; A61B 5/37; A61B 5/301; A61B 5/31; A61B 5/7225;
(Continued)

(56) References Cited

U.S. PATENT DOCUMENTS 5,683,422 A 11/1997 Rise
6,066,163 A 5/2000 John
(Continued)

FOREIGN PATENT DOCUMENTS

WO WO 2004/052449 6/2004
WO WO 2015/149170 10/2015
(Continued)

OTHER PUBLICATIONS

Asaridou et al., "Stimulating the Semantic Network: What Can TMS Tell Us about the Roles of the Posterior Middle Temporal Gyrus and Angular Gyrus?," J. Neuroscience, Apr. 2016, 36(16):4405-4407.
(Continued)

*Primary Examiner* — Jean B Jeanglaude
(74) *Attorney, Agent, or Firm* — Fish & Richardson P.C.

(57) ABSTRACT

This specification discloses a brain electrode device. The brain electrode device includes a set of contact points and a set of sub-circuits. The sub-circuits include sensor ports configured to connect to the contact to the respective ones of the contact points. The device can further include an intelligent multiplexer that aggregates signals from the set of sub-circuits and generates an aggregate signal. The aggregate signal is transmitted to a signal acquisition device.

9 Claims, 12 Drawing Sheets

(58) Field of Classification Search
CPC .... A61B 5/293; A61N 1/025; A61N 1/36025; A61N 1/0476
USPC ........................................................ 341/155
See application file for complete search history.

(56) References Cited

U.S. PATENT DOCUMENTS

| | | | |
|---|---|---|---|
| 7,299,096 | B2 | 11/2007 | Balzer et al. |
| 8,150,524 | B2 | 4/2012 | Maschino et al. |
| 10,617,348 | B2 * | 4/2020 | Howard ............... A61B 5/055 |
| 2003/0097159 | A1 | 5/2003 | Schiff et al. |
| 2005/0033378 | A1 | 2/2005 | Sheffield et al. |
| 2007/0055320 | A1 | 3/2007 | Weinand |
| 2010/0036211 | A1 | 2/2010 | La Rue et al. |
| 2012/0016430 | A1 | 1/2012 | Lozano |
| 2013/0245486 | A1 | 9/2013 | Simon et al. |
| 2014/0025133 | A1 | 1/2014 | Lozano |
| 2014/0148872 | A1 | 5/2014 | Goldwasser et al. |
| 2015/0080695 | A1 | 3/2015 | Rogers et al. |
| 2015/0174403 | A1 | 6/2015 | Pal et al. |
| 2015/0367133 | A1 | 12/2015 | Schiff et al. |
| 2017/0042474 | A1 | 2/2017 | Widge et al. |
| 2017/0043167 | A1 | 2/2017 | Widge et al. |
| 2017/0249853 | A1 | 8/2017 | Weiss et al. |
| 2018/0001077 | A1 | 1/2018 | Cook et al. |
| 2018/0021579 | A1 | 1/2018 | Kahana et al. |
| 2018/0333587 | A1 | 11/2018 | Howard |
| 2019/0150774 | A1 | 5/2019 | Brinkmann et al. |
| 2019/0282815 | A1 | 9/2019 | Kahana et al. |
| 2021/0031044 | A1 | 2/2021 | Kucewicz et al. |

FOREIGN PATENT DOCUMENTS

| | | |
|---|---|---|
| WO | WO 2015/191628 | 12/2015 |
| WO | WO 2017/196971 | 11/2017 |
| WO | WO 2018/017655 | 1/2018 |
| WO | WO 2019/079378 | 4/2019 |
| WO | WO 2019/183046 | 9/2019 |

OTHER PUBLICATIONS

Benchohra et al., "Existence results for boundary value problems with non-linear fractional differential equations," Appl. Analysis, Jul. 2008, 87(7):851-863.

Bickford et al., "Changes in memory function produced by electrical stimulation of the temporal lobe in man," Res. Publ. Assoc. Res. Nerv. Ment. Disease, 1958, 36:227-243.

Binder et al., "Where Is the Semantic System? A Critical Review and Meta-Analysis of 120 Functional Neuroimaging Studies," Cereb. Cortex, Dec. 2009, 19(12):2767-2796.

Bokil et al., "Chronux: A platform for analyzing neural signals," J. Neurosci. Methods, Sep. 2010, 192(1):146-151.

Borchers et al., "Direct electrical stimulation of human cortex—the gold standard for mapping brain functions?" Nat. Rev. Neuroscience, Jan. 2012, 13(1):63-70.

Burke et al., "Human intracranial high-frequency activity maps episodic memory formation in space and time," NeuroImage, Jan. 2014, 85(Part 2):834-843.

Chang, "Towards Large-Scale, Human-Based, Mesoscopic Neurotechnologies," Neuron, Apr. 8, 2015, 86(1):68-78.

Coleshill et al., "Material-Specific Recognition Memory Deficits Elicited by Unilateral Hippocampal Electrical Stimulation," J. Neuroscience, Feb. 18, 2004, 24(7):1612-1616.

Doleǎl et al., "Application of eye tracking in neuroscience," Clin. Neurophysiology, Mar. 2015, 126(3):e44, 1 page.

Dykstra et al., "Individualized localization and cortical surface-based registration of intracranial electrodes," NeuroImage, Feb. 2012, 59(4):3563-3570.

Eichenbaum et al., "A cortical-hippocampal system for declarative memory," Nat. Rev. Neuroscience, Oct. 2000, 1(1):41-50.

Einhäuser et al., "Pupil dilation betrays the timing of decisions," Front. Hum. Neuroscience, Feb. 26, 2010, 4:18, 9 pages.

Einhäuser et al., "Pupil dilation reflects perceptual selection and predicts subsequent stability in perceptual rivalry," Proc. Nat. Acad. Sci. USA, Feb. 5, 2008, 105(5):1704-1709.

Epstein et al., "Development and Testing of an Instrument to Measure Moral Distress in Healthcare Professionals," AJOB Primary Research, Apr. 2012, 3(2):1-9.

Ezzyat et al., "Closed-loop stimulation of temporal cortex rescues functional networks and improves memory," Nat. Communications, Feb. 6, 2018, 9:365, 8 pages.

Ezzyat et al., "Direct Brain Stimulation Modulates Encoding States and Memory Performance in Humans," Curr. Biology, May 8, 2017, 27(9):1251-1258.

Fell et al., "Memory Modulation by Weak Synchronous Deep Brain Stimulation: A Pilot Study," Brain Stimulation, May 2013, 6(3):270-273.

Fischl et al., "Automatically Parcellating the Human Cerebral Cortex," Cereb. Cortex, Jan. 2004, 14(1):11-22.

Foundations of Human Memory, 1st ed., Kahana (ed.), May 2012, 364 pages.

Fried et al., "Memory Enhancement and Deep-Brain Stimulation of the Entorhinal Area," N. Engl. J. Medicine, Feb. 9, 2012, 366(6):502-510.

Hamani et al., "Memory Enhancement Induced by Hypothalamic/Fornix Deep Brain Stimulation," Ann. Neurology, Jan. 2008, 63(1):119-123.

Heaver et al., "Keeping an eye on the truth? Pupil size changes associated with recognition memory," Memory, May 2011, 19(4):398-405.

Hess et al., "Pupil size as related to interest value of visual stimuli," Science, Aug. 1960, 132(3423):349-350.

Hess et al., "Pupil Size in Relation to Mental Activity during Simple Problem-Solving," Science, Mar. 1964, 143(3611):1190-1192.

Histed et al., "Direct Activation of Sparse, Distributed Populations of Cortical Neurons by Electrical Microstimulation," Neuron, Aug. 27, 2009, 63(4):508-522.

Horak et al., "Interictal epileptiform discharges impair word recall in multiple brain areas," Epilepsia, Mar. 2017, 58(3):373-380.

Jacobs et al., "Direct Electrical Stimulation of the Human Entorhinal Region and Hippocampus Impairs Memory," Neuron, Dec. 7, 2016, 92(5):983-990.

Jensen et al., "Human gamma-frequency oscillations associated with attention and memory," Trends in Neurosciences, Jul. 2007, 30(7):317-324.

Johnson et al., "Neuromodulation for Brain Disorders: Challenges and Opportunities," IEEE Trans. Biomed. Engineering, Mar. 2013, 60(3):610-624.

Jutras et al., "Oscillatory activity in the monkey hippocampus during visual exploration and memory formation," Proc. Natl. Acad. Sci. USA, Aug. 2013, 110(32):13144-13149.

Kahana et al., "Biomarker-guided neuromodulation aids memory in traumatic brain injury," medRxiv, May 22, 2021, 16 pages.

Kahana, "The Cognitive Correlates of Human Brain Oscillations," J. Neuroscience, Feb. 8, 2006, 26(6):1669-1672.

Kahneman et al., "Pupil Diameter and Load on Memory," Science, Dec. 1966, 154(3756):1583-1585.

Kim et al., "A network approach for modulating memory processes via direct and indirect brain stimulation: toward a causal approach for the neural basis of memory," Neurobiol. Learn. Memory, Oct. 2016, 134(Part A):162-177.

Kim, "Neural activity that predicts subsequent memory and forgetting: a meta-analysis of 74 fMRI studies," NeuroImage, Feb. 2011, 54(3):2446-2461.

Kucewicz et al., "Evidence for verbal memory enhancement with electrical brain stimulation in the lateral temporal cortex," Brain, Apr. 2018, 141(4):971-978.

Kucewicz et al., "High frequency oscillations are associated with cognitive processing in human recognition memory," Brain, Jun. 2014, 137:2231-2244.

Kucewicz et al., "Pupil size reflects successful encoding and recall of memory in humans," Sci. Reports, Mar. 21, 2018, 8(1):4949, 7 pages.

(56) References Cited

OTHER PUBLICATIONS

Kurzweilai.net [online], "Recording data from one million neurons in real time," dated Mar. 23, 2018, retrieved on Mar. 26, 2018, retrieved from URL<http://www.kurzweilai.net/recording-data-from-one-million-neurons-in-real-time>, 4 pages.

Lachaux et al., "High-frequency neural activity and human cognition: Past, present and possible future of intracranial EEG research," Prog. Neurobiology, Sep. 2012, 98(3):279-301.

Leonard et al., "Sharp Wave Ripples during Visual Exploration in the Primate Hippocampus," J. Neurosci., Nov. 2015, 35(44):14771-14782.

Leonard et al., "Sharp-Wave Ripples in Primates Are Enhanced near Remembered Visual Objects," Curr. Biology, Jan. 2017, 27(2):257-262.

LLNL.gov [online], "NIH taps Lab to develop sophisticated electrode array system to monitor brain activity," dated Sep. 30, 2014, retrieved on Apr. 2, 2018, retrieved from URL<https://www.llnl.gov/news/nih-taps-lab-develop-sophisticated-electrode-array-system-monitor-brain-activity>, 5 pages.

McCormick, "Cholinergic and noradrenergic modulation of thalamocortical processing," Trends in Neurosciences, Jan. 1989, 12(6):215-221.

McCreery et al., "Charge density and charge per phase as cofactors in neural injury induced by electrical stimulation," IEEE Trans. Biomed. Engineering, Oct. 1990, 37(10):996-1001.

McGinley et al., "Cortical Membrane Potential Signature of Optimal States for Sensory Signal Detection," Neuron, Jul. 1, 2015, 87(1):179-192.

Miller et al., "Visual-spatial memory may be enhanced with theta burst deep brain stimulation of the fornix: a preliminary investigation with four cases," Brain, Jul. 2015, 138:1833-1842.

Montgomery et al., "Gamma oscillations dynamically couple hippocampal CA3 and CA1 regions during memory task performance," Proc. Nat. Acad. Sci. USA, Sep. 2007, 104(36):14495-14500.

Musk et al., "An Integrated Brain-Machine Interface Platform with Thousands of Channels," bioRxiv, Jul. 16, 2019, 12 pages.

Naber et al., "Pupil size signals novelty and predicts later retrieval success for declarative memories of natural scenes," J. Vision, Feb. 2013, 13(2):11, 20 pages.

NIH.gov [online], "Brain Stimulation Therapies," available on or before Dec. 6, 2009 via Internet Archive: Wayback Machine URL<https://web.archive.org/web/20091206111859/https://www.nimh.nih.gov/health/topics/brain-stimulation-therapies/brain-stimulation-therapies.shtml>, retrieved on Jul. 11, 2022, retrieved from URL<https://www.nimh.nih.gov/health/topics/brain-stimulation-therapies/brain-stimulation-therapies.shtml>, 8 pages.

Ojemann et al., "Cortical language localization in left, dominant hemisphere: an electrical stimulation mapping investigation in 117 patients," J. Neurosurgery, Sep. 1989, 71(3):316-326.

Otero et al., "Pupil size changes during recognition memory," Psychophysiology, Oct. 2011, 48(10):1346-1353.

PCT International Preliminary Report on Patentability in International Appln. No. PCT/US2020/060408, dated May 17, 2022, 9 pages.

PCT International Search Report and Written Opinion in International Appln. No. PCT/US2020/060408, dated Feb. 5, 2021, 10 pages.

Penfield et al., "The brain's record of auditory and visual experience: a final summary and discussion," Brain, Dec. 1963, 86(4):595-696.

Perlmutter et al., "Deep Brain Stimulation," Annu. Rev. Neuroscience, 2006, 29:229-257.

Raghavachari et al., "Theta Oscillations in Human Cortex During a Working-Memory Task: Evidence for Local Generators," J. Neurophysiology, Mar. 2006, 95(3):1630-1638.

Reimer et al., "Pupil fluctuations track rapid changes in adrenergic and cholinergic activity in cortex," Nat. Communications, Nov. 2016, 7:13289, 7 pages.

Sahakian et al., "The impact of neuroscience on society: cognitive enhancement in neuropsychiatric disorders and in healthy people," Phil. Trans. R. Society B, Sep. 2015, 370(1677):20140214, 13 pages.

Sederberg et al., "Gamma Oscillations Distinguish True From False Memories," Psychol. Science, Nov. 2007, 18(11):927-932.

Sederberg et al., "Hippocampal and Neocortical Gamma Oscillations Predict Memory Formation in Humans," Cereb. Cortex, May 2007, 17(5):1190-1196.

Starc et al., "Fine-grained versus categorical: Pupil size differentiates between strategies for spatial working memory performance," Psychophysiology, May 2017, 54(5):724-735.

Sternberg, "High-Speed Scanning in Human Memory," Science, Aug. 1966, 153(3736):652-654.

Suthana et al., "Deep brain stimulation for enhancement of learning and memory," NeuroImage, Jan. 2014, 85:996-1002.

Suthana et al., "Memory Enhancement and Deep-Brain Stimulation of the Entorhinal Area," N. Engl. J. Medicine, Feb. 2012, 366(6):502-510.

Tallon-Baudry et al., "Oscillatory gamma activity in humans and its role in object representation," Trends Cogn. Sciences, Apr. 1999, 3(4):151-162.

UCL.ac.uk [online], "Development," available on or before Mar. 25, 2017 via Internet Archive: Wayback Machine URL<https://web.archive.org/web/20170325173240/http://www.ucl.ac.uk/neuropixels/development>, retrieved on Apr. 2, 2018, retrieved from URL<http://www.ucl.ac.uk/neuropixels/development>, 1 page.

UCL.ac.uk [online], "Neuropixels," available on or before Mar. 25, 2017 via Internet Archive: Wayback Machine URL<https://web.archive.org/web/20170325111139/http://www.ucl.ac.uk/neuropixels>, retrieved on Mar. 26, 2018, retrieved from URL<http://www.ucl.ac.uk/neuropixels>, 2 pages.

Underwood, "Researchers aim for an electrical memory prosthesis," Science, Jul. 18, 2014, 345(6194):250.

Van Gompel et al., "Phase I trial: safety and feasibility of intracranial electroencephalography using hybrid subdural electrodes containing macro- and microelectrode arrays," Neurosurg. Focus, Sep. 2008, 25(3):E23, 6 pages.

Vo et al., "The coupling of emotion and cognition in the eye: Introducing the pupil old/new effect," Psychophysiology, Jan. 2008 45(1):130-140.

Worrell et al., "Recording and analysis techniques for high-frequency oscillations," Prog. Neurobiology, Sep. 2012, 98(3):265-278.

Yushkevich et al., "Automated Volumetry and Regional Thickness Analysis of Hippocampal Subfields and Medial Temporal Cortical Structures in Mild Cognitive Impairment," Hum. Brain Mapping, Jan. 2015, 36(1):258-287.

\* cited by examiner

SCALABLE MULTI-RESOLUTION ELECTRODE ARRAY FOR SENSING AND STIMULATING THE BRAIN

CROSS-REFERENCE TO RELATED APPLICATIONS

This application is a National Stage application under 35 U.S.C. § 371 of International Application No. PCT/US2020/060408, having an International Filing Date of Nov. 13, 2020, which claims the benefit of priority to U.S. Application Ser. No. 62/935,400, filed on Nov. 14, 2019. The content of U.S. Application Ser. No. 62/935,400 is considered part of the disclosure of the present document and is incorporated by reference in its entirety.

BACKGROUND

1. Technical Field

This document describes devices, systems, and methods related to electrode arrays for sensing and/or stimulating a brain of a mammal (e.g., a human) or other animal.

2. Background Information

Electroencephalography (EEG) is a method for sensing the electrical activity within the brain. EEG can be noninvasive where electrodes are placed on the scalp, or it can be invasive where the electrodes are placed directly on the brain. Some electrodes are placed on the surface of the scalp or brain (i.e. cortex), while other probes penetrate into the brain tissue. EEG is used to detect and diagnose a variety of ailments, including epilepsy, encephalitis, stroke, sleep disorders, and dementia.

Beyond clinical diagnosis and treatment, there is growing interest in brain-machine interfaces whereby the brain is able to interact with external machines such as computers. Both noninvasive and invasive electrodes are showing promise of enabling human thought to control external systems and conversely external systems to influence human thought. Electrodes that make electrical contact with the brain are required to enable the brain-machine interface.

SUMMARY

Some embodiments described herein include an electroencephalography (EEG) electrode system for sensing and/or stimulating a brain while reducing risk associated with the sensing and stimulation. In some implementations, the electrode system can be an electroencephalography (EEG) electrode system. In other implementations, the same electrode system can be used in non-EEG applications, such as within a brain-machine interface. The system is scalable to different numbers of contacts to span large areas of the brain. For example, the system includes an EEG electrode array made with a plurality of patches connected together physically and electrically. In some implementations, each patch can have its own respective intelligent multiplexer and/or intelligent demultiplexer to aggregate the respective sense and/or stimulate signals. Alternatively or in addition, the electrode array can include an application-wide intelligent multiplexer and/or intelligent demultiplexer to subsequently aggregate the signals for each patch, thereby reducing the wire or lead count down to a single wire or wireless link. In some implementations, each patch, or the array as a whole, can have an embedded ground plane, thus minimizing the susceptibility to external electromagnetic (EM) noise or interference. Moreover, the physical resolution of each patch, or the array at a whole, can be adjusted as needed.

Particular embodiments described herein include a brain electrode device including a plurality of contact points, a plurality of sub-circuits, and a plurality of sub-circuits. The plurality of sub-circuits includes sensor ports configured to connect to the contact points, respectively. The plurality of sub-circuits is configured to aggregate signals from the plurality of sub-circuits and generate an aggregate signal. The aggregate signal may be transmitted to a signal acquisition device.

In some implementations, the system can optionally include one or more of the following features. The plurality of sub-circuits may include sample/hold circuits configured to sample respective input signals and hold its value. The brain electrode device may further include a snapshot signal circuit configured to instruct the sample/hold circuits with timings of sampling the input signals. The snapshot signal may be configured to reset the sample/hold circuits during a next snapshot pulse. The signal acquisition system may include an analog-to-digital converter and a digital signal processor.

Particular embodiments described herein include a method for sensing signals from a brain. The method may include one or more of the following processes: engaging an electrode array with the brain, the electrode array including a plurality of cells; sampling signals at the respective cells; aggregating, using an intelligent multiplexer, the signals; and transmitting an aggregated signal to a signal acquisition circuit for processing.

In some implementations, the system can optionally include one or more of the following features. The method may further includes holding the signals at the respective cells. The method may further include time-aligning the signals prior to aggregating the signals. The time-aligning the signals may include injecting a snapshot signal to the cells, the snapshot signal configured to control timings of sampling the signals at the respective cells.

Particular embodiments described herein include a brain electrode device including a plurality of contact points, a plurality of sub-circuits, and an intelligent demultiplexer. The plurality of sub-circuits may include sensor ports configured to connect to the contact points, respectively. The intelligent demultiplexer may be configured to accept an input signal an aggregate of signals from a control device. The input signal may be an aggregate of signals. The intelligent demultiplexer may be configured to distribute the signals in the input signal to their respective destinations.

Particular embodiments described herein include a brain electrode device including a plurality of contact points, a plurality of sub-circuits, a plurality of adder circuits, and an intelligent multiplexer. The plurality of sub-circuits may include sensor ports configured to connect to the contact points, respectively. Each of the plurality of adder circuits may be configured to aggregate signals from a group of sub-circuits and generate an adder aggregate signal. The group may be selected from the plurality of sub-circuits. The intelligent multiplexer may be configured to aggregate signals directly from the plurality of sub-circuits, or aggregate the adder aggregate signals from the adder circuits. The intelligent multiplexer may be configured to generate an aggregate signal being transmitted to a signal acquisition device.

In some implementations, the system can optionally include one or more of the following features. The plurality of sub-circuits may include sample/hold circuits configured to sample respective input signals and hold its value. The brain electrode device may further include a snapshot signal circuit configured to instruct the sample/hold circuits with timings of sampling the input signals. The snapshot signal may be configured to reset the sample/hold circuits during a next snapshot pulse. The signal acquisition system may include an analog-to-digital converter and a digital signal processor.

Particular embodiments described herein include a method for sensing signals from a brain. The method may may include one or more of the following processes: engaging an electrode array with the brain, the electrode array including a plurality of cells and groups of cells being selected from the plurality of cells; sampling signals at the respective cells; aggregating, using each of a plurality of adder circuits, signals from each of the groups of cells to generate a first aggregate signal; aggregating, using an intelligent multiplexer, the first aggregate signals from the plurality of adder circuits to generate a second aggregate signal; and transmitting the second aggregate signal to a signal acquisition circuit for processing.

In some implementations, the system can optionally include one or more of the following features. The method may further include aggregating, using the intelligent multiplexer, the signals from the cells; and transmitting the aggregated signal to the signal acquisition circuit. The method may further include holding the signals at the respective cells. The method may further include time-aligning the signals prior to aggregating the signals. Time-aligning the signals may include injecting a snapshot signal to the cells, the snapshot signal configured to control timings of sampling the signals at the respective cells.

Particular embodiments described herein include a brain electrode device including an electrode array membrane, a plurality of fine-resolution contact points, and a coarse-resolution contact point. The plurality of fine-resolution contact points may be distributed in an array across a surface of the electrode array membrane. The coarse-resolution contact point may include a perforated plate. The plate may have a plurality of holes within which the plurality of fine-resolution contact points are disposed.

Particular embodiments described herein include a brain electrode device including a sensing circuit and a stimulating circuit. The sensing circuit may include a plurality of first contact points, a plurality of first sub-circuits, and an intelligent multiplexer. The plurality of first sub-circuits may include sensor ports configured to connect to the first contact points, respectively. The intelligent multiplexer may be configured to aggregate signals from the plurality of first sub-circuits and generate an aggregate signal. The aggregate signal may be transmitted to a signal acquisition device. The stimulating circuit may include a plurality of second contact points, a plurality of second sub-circuits, and an intelligent demultiplexer. The plurality of second sub-circuits may include sensor ports configured to connect to the second contact points, respectively. The intelligent demultiplexer may be configured to receive a single stimulation signal from a controller and generate a plurality of sub-stimulation signals being transmitted to the plurality of second sub-circuits.

In some implementations, the system can optionally include one or more of the following features. The sensing and the stimulating circuit may be operated independently. The sensing circuit and the simulating circuit may be simultaneously operated. The plurality of sub-circuits may include sample/hold circuits configured to sample an input signal and hold its value. The brain electrode device may further include a snapshot signal circuit configured to transmit a snapshot signal to instruct the sample/hold circuits with timings of sampling the input signals. The snapshot signal may be configured to reset the sample/hold circuits during a next snapshot pulse. The signal acquisition system may include an analog-to-digital converter and a digital signal processor.

Particular embodiments described herein include a method for sensing signals from a brain and stimulating the brain. The method may include one or more of the following processes: engaging an electrode array with the brain, the electrode array including a plurality of cells; sensing signals from the brain by sampling signals at the respective cells; aggregating, using an intelligent multiplexer, the signals; and transmitting an aggregated signal to a signal acquisition circuit for processing; stimulating the brain by obtaining a stimulation signal; generating, using an intelligent demultiplexer, a plurality of sub-stimulation signals from the stimulation signal; and transmitting the plurality of sub-stimulation signals to the plurality of cells. Sensing the signals from the brain may be performed simultaneously with stimulating the brain. Sensing the signals from the brain may further include holding the signals at the respective cells. Sensing the signals from the brain may further include time-aligning the signals prior to aggregating the signals. Time-aligning the signals may include injecting a snapshot signal to the cells, the snapshot signal configured to control timings of sampling the signals at the respective cells.

Particular embodiments described herein include a brain electrode device including a plurality of patches, and an intelligent multiplexer. The plurality of patches may be movably connected in array. Each patch may include a plurality of contact points, and a sub-circuit including a sensor port configured to connect to the contact points. The intelligent multiplexer may be configured to aggregate patch signals from the plurality of contact points into an aggregate signal. The aggregate signal may be transmitted to a signal acquisition device.

In some implementations, the system can optionally include one or more of the following features. Each patch may include a tab and a slot configured to receive a tab from an adjoining patch. Each patch may include a plurality of tabs at an end and a plurality of slots at another end and configured to receive a plurality of tabs from an adjoining patch. The tabs of the patch are attached to the adjoining patch using adhesive. The tabs of the patch may be attached to the adjoining patch using a fastener. Each path may include a patch multiplexer configured to aggregate signals from the sub-circuit in the patch and generate a patch signal. The tabs may be flexible. The tabs may include electronics thereon and are configured to isolate the electronics from a brain tissue to which the plurality of patches is engaged. The electronics may include the intelligent multiplexer. The brain electrode device may further include marks provided on the tabs and configured to measure an effective insertion distance of the tabs.

Particular embodiments described herein include a brain electrode device including a plurality of contact points, a plurality of sub-circuits, a ground electrode wire, and a signal electrode wire. The plurality of sub-circuits may include sensor ports configured to connect to the contact points, respectively. The signal electrode wire may be routed parallel with the ground electrode wire and spaced apart from the ground electrode wire at a predetermined distance.

In some implementations, the system can optionally include one or more of the following features. The predetermined distance may range between 1 micron and 10 millimeters. The brain electrode device may further include an intelligent multiplexer configured to aggregate signals from the plurality of sub-circuits and generate an aggregate signal. The aggregate signal may be transmitted to a signal acquisition device. The plurality of sub-circuits may include sample/hold circuits configured to sample an input signal and hold its value. The brain electrode device may further include a snapshot signal circuit configured to transmit a snapshot signal to instruct the sample/hold circuits with timings of sampling the input signals. The snapshot signal may be configured to reset the sample/hold circuits during a next snapshot pulse. The signal acquisition system may include an analog-to-digital converter and a digital signal processor.

The devices, system, and techniques described herein may provide one or more of the following advantages. Some embodiments described herein include EEG electrode arrays with an intelligent multiplexer for aggregating signals from multiple contact points, thereby reducing the wire count between the electrode array and an external signal acquisition system, and further reducing the extent of the external acquisition system, thus enabling massive scaling of the quantity of contact points.

Also, some embodiments of the EEG electrode arrays include intelligent multiplexers or intelligent demultiplexers that enable real-time sub-sampling or sub-stimulation, respectively, of the available contacts to control the amount of available data or vary the effective contact density within specific regions of the brain.

Further, some embodiments of the EEG electrode arrays disclosed herein are configured to adapt their physical resolution from wide pitch (for identifying the general area of interest) to fine pitch (for pinpointing the location for treatment) in such a way to eliminate the need to physically replace electrode arrays and thus reduce risk to the patient.

Addition, some embodiments of the EEG electrode arrays enable multiple contacts to be electrically tied together to reduce the effective contact resistance between the contacts and the brain, thereby improving the resulting signal quality.

Moreover, some embodiments of the EEG electrode arrays disclosed herein provide the ability to both sense and stimulate signals with one electrode array, thereby reducing risk to the patient simply due to the elimination of need to apply/remove/reapply electrodes for the different purposes. In addition, such arrays can further provide the ability to perform real-time, closed-loop treatment to patients so that the patient's condition can be continually monitored (sensed) during treatment (stimulated), which enables more precise and safer treatment.

In addition, some embodiments disclosed herein include EEG electrode arrays having multiple patches configured to conform to the brain's three-dimensional shape without degradation of contact resistance or harm to the patient. These same patches can be tacked together to ensure they stay physically stable relative to one another, thus improving repeatability between different applications of the electrode arrays.

Further, some embodiments of EEG electrode arrays have ground planes within and between patches to increase immunity to external EM noise, thus improving the quality of electrical signal and patient care.

The details of one or more implementations are set forth in the accompanying drawings and the description below. Other features and advantages will be apparent from the description and drawings, and from the claims.

DETAILED DESCRIPTION

Figure 1:
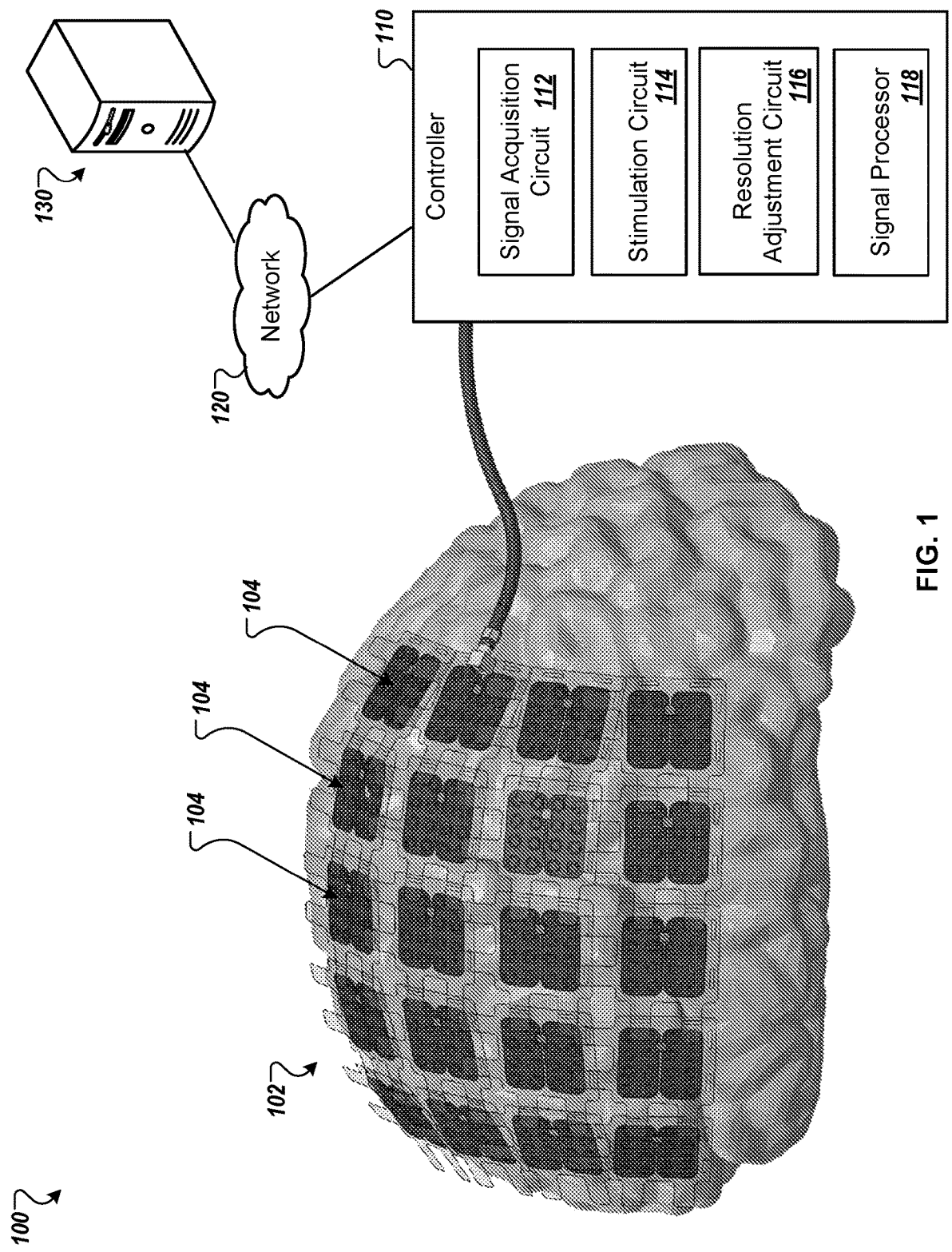
FIG. 1 illustrates an example system with an EEG electrode array that can cover an outer surface of the brain.

Referring to FIG. 1, an example system 100 is described which includes an EEG electrode array 102 that can cover an outer surface of the brain (or cortex). As described herein, the EEG electrode array 102 can be modular and easily adapted to different shapes and sizes, such as a size that covers the entire outer surface of the brain's cortex or a size that covers a smaller region of the surface of the brain. In some implementations, the EEG electrode array 102 can be made with a plurality of patches 104 which may be connected together physically (e.g., mechanically), electrically, or both. As described in more detail with reference to FIG. 10, the patches 104 can be connected through tabs and slots (e.g., one or more tabs on each of a plurality of sides, and one or more slots on each of the other plurality of sides).

In some implementations, each patch 104 has its own respective circuitry for an intelligent multiplexer (as described in FIGS. 2-6) and/or intelligent demultiplexer (as described in FIGS. 7-9) to aggregate the respective sense and/or stimulate signals. In addition or alternatively, the electrode array 102 can include circuitry for an application-wide intelligent multiplexer (as described in FIGS. 2-6) and/or intelligent demultiplexer (as described in FIGS. 7-9) to subsequently aggregate the signals for each patch, thereby reducing the wire count down to a single wire or wireless link.

In some implementations, each patch 104 has an embedded ground plane (not shown) (as described in FIG. 11) that can be interconnected to the ground planes in the surrounding patches through the tabs, thus minimizing the susceptibility to external EM noise.

Figure 4:
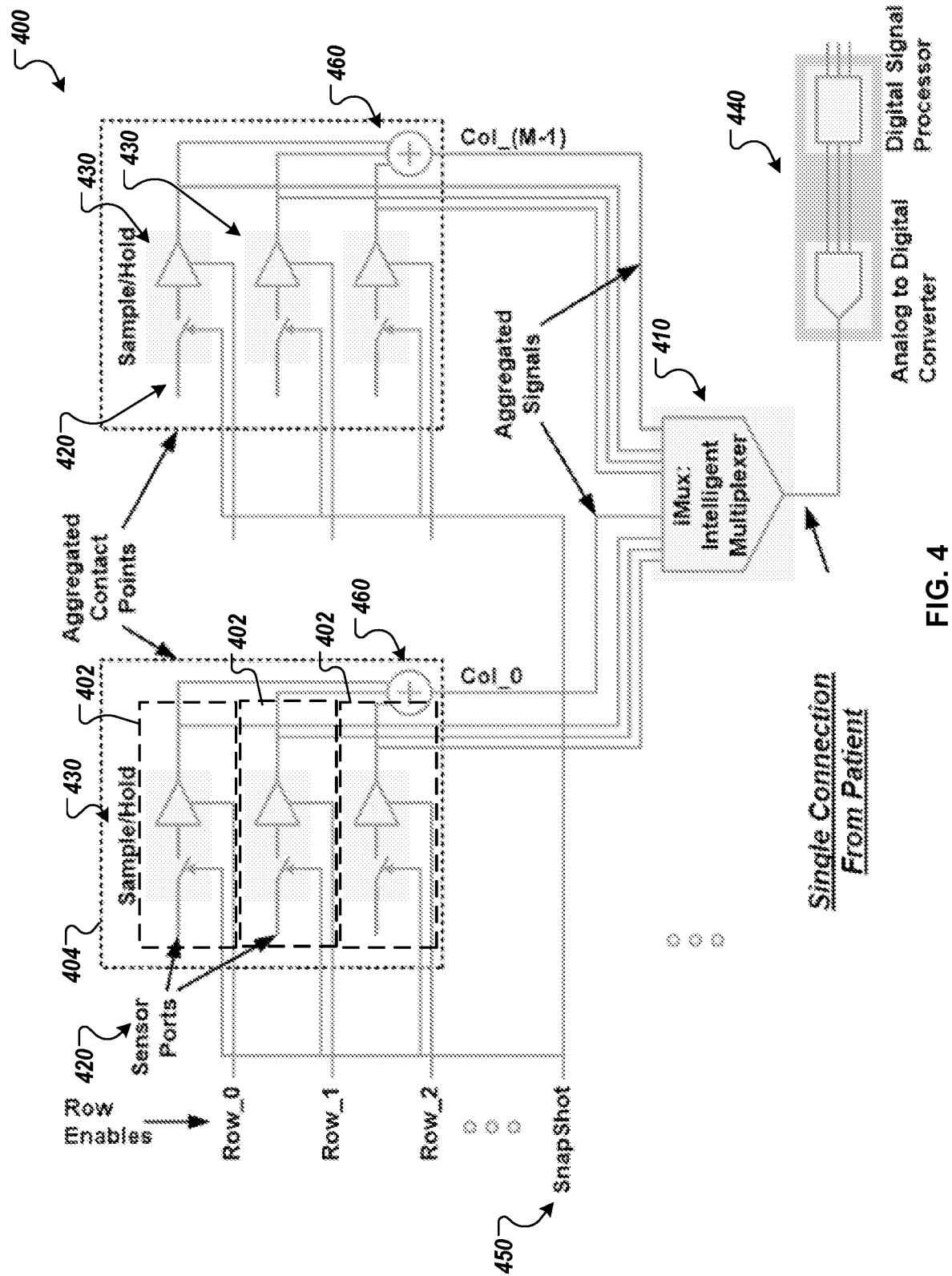
FIG. 4 illustrates an example EEG electrode array.
Figure 5:
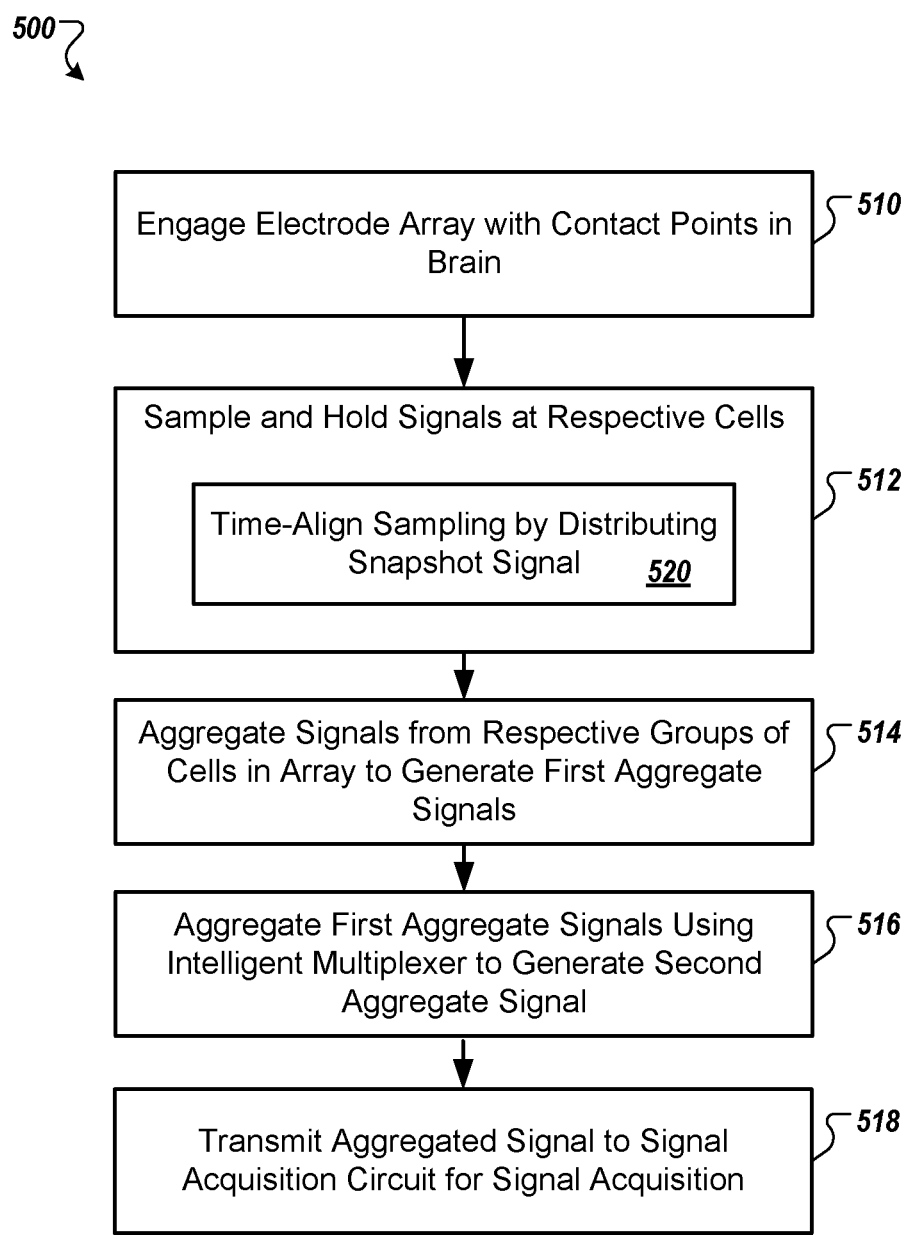
FIG. 5 is a flowchart of an example process for acquiring signals from a brain using an electrode array.
Figure 6:
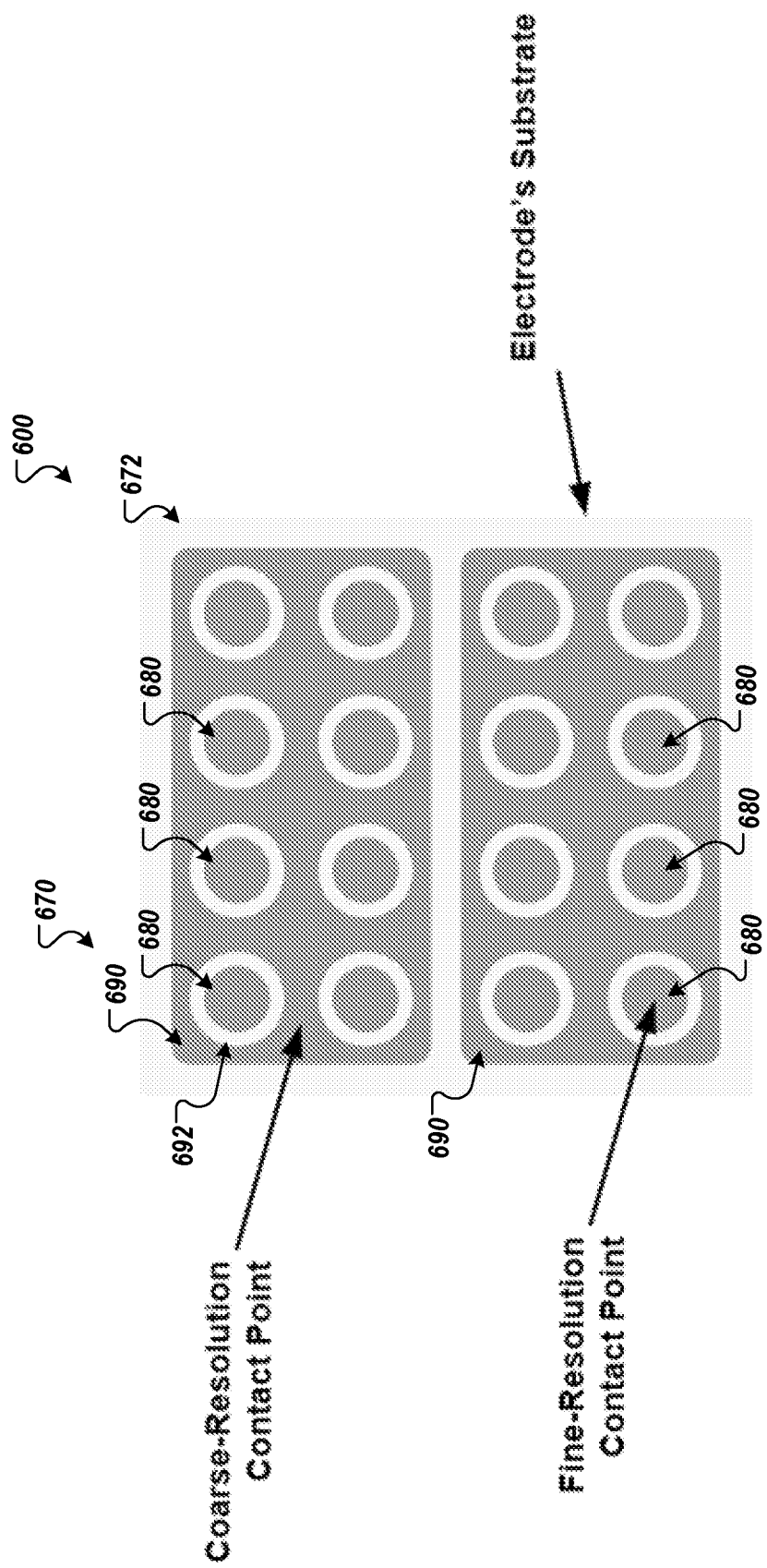
FIG. 6 illustrates a zoomed-in view of contact points on an electrode array membrane.

Each patch can have both sensing and stimulation capabilities, and the physical resolution can be adjusted as needed, as described in FIGS. 4-6.

The system 100 can further include a controller 110 for controlling the EEG electrode array 102. The controller 110 can provide several modules or circuits, such as a signal acquisition circuit 112 for acquiring an aggregate signal from the array 102, a stimulation circuit 114 for transmitting a stimulation signal to all or some of the patches 104 in the array 102, a resolution adjustment circuit 116 for adjusting sensing/stimulating resolutions of the array 102 (e.g., between wide pitch and fine pitch or sub-sample some of the available contact points), and a signal processor 118 for processing signals acquired from, and transmitted to, the array 102. In some implementations, the controller 110 can be connected to a remote computing device or server 130 via a network 120. The remote computing device or server 130 can receive data from the controller 110 for further analysis, management, storage, and transmission of data to the controller 110 for controlling and managing the controller 110 and the array 102 connected to the controller 110.

EEG Electrode Circuit with Intelligent Multiplexer and Sample/Hold

Figure 2:
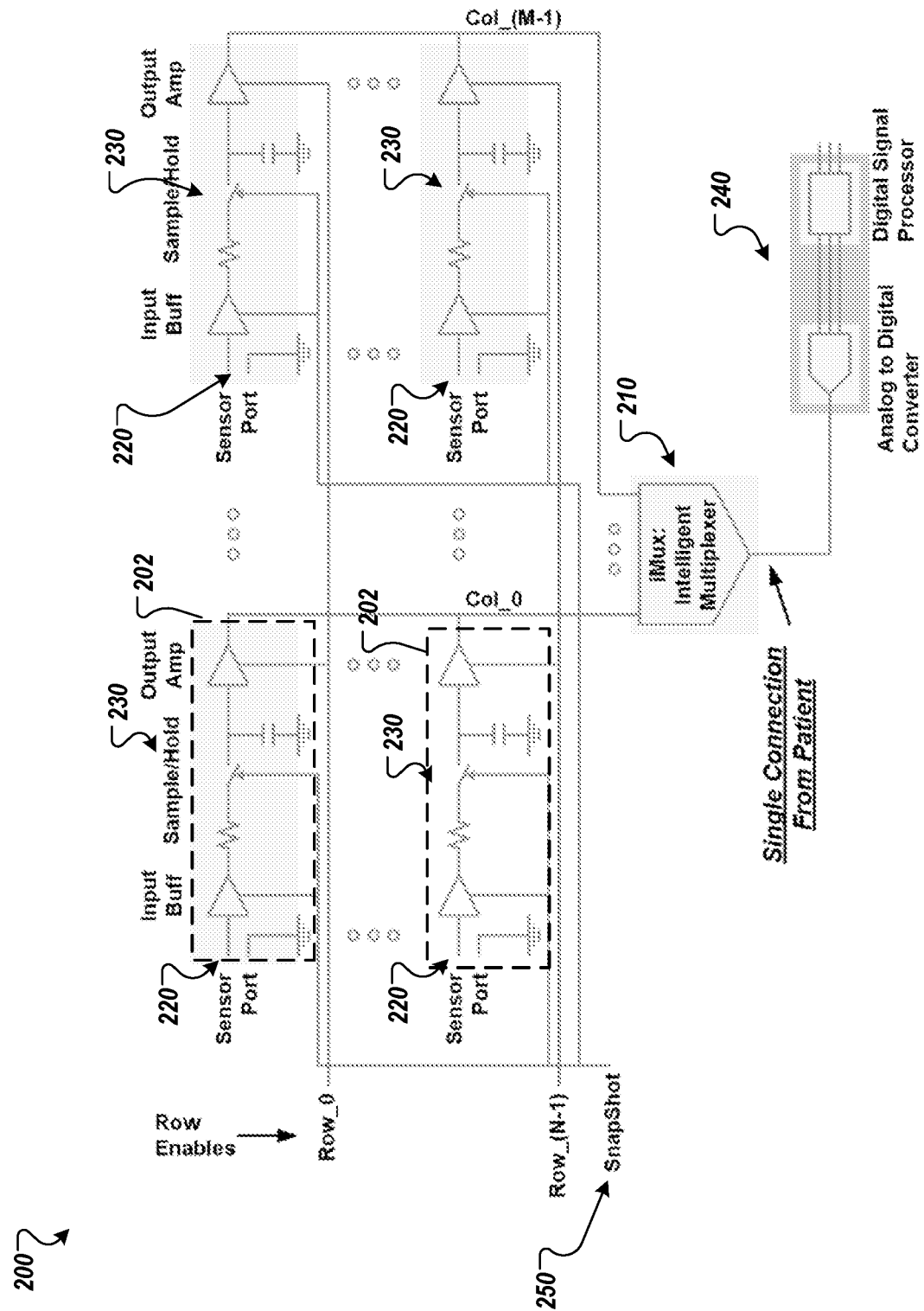
FIG. 2 illustrates a circuit diagram of an example EEG electrode array circuit.

FIG. 2 illustrates a circuit diagram of an example EEG electrode array circuit 200. In some embodiments, through use of a multiplexer, the electrode array circuit 200 can reduce the quantity of wires between the electrode array's contact points and an external acquisition system.

In general, an example EEG apparatus may include electrodes that make electrical contact with a scalp or brain. For example, such electrodes can have single contact points, and each single-point electrode can have a respective discrete wire to an external signal acquisition system. In another example, an EEG apparatus may include electrodes that have arrays of contact points that are patterned across the surface of a flexible membrane. Such electrode arrays may use metal disks for the contacts. The metal is a good electrical conductor, and the physical thickness of the disk protrudes outward from the substrate's surface to reduce the electrical contact resistance. From each disk, a wire is routed on the surface of or within the electrode array to a connector along the electrode's edge, which is subsequently used to connect to an external signal acquisition system.

In yet another example, an EEG apparatus may be configured to attach a dedicated wire between each of the contact points and the external signal acquisition system. By doing so, each contact point can be independently and simultaneously acquired. However, this method constrains scalability due to the physical size and weight of the wires and due to the cost of the equipment needed to acquire each of the signals independently. For example, a high density electrode array may include 256 contacts (e.g., arranged as a 16 by 16 array). The corresponding 256 copper wires of such an array can physically weigh multiple kilograms (pounds) and have an aggregate diameter of approximately 5 cm (2 inch). The massive bundle of wires can be cumbersome and severely limit patient mobility, can pose physical risks to the patient, and can preclude peripheral access to and treatment of the brain.

The signal acquisition equipment may also be comparably expensive. After the basic framework is in place, each contact point within the electrode array requires a corresponding copper wire, connector, analog to digital converter (ADC), and signal processor. Roughly speaking, doubling the quantity of contact points approximately doubles the cost of the acquisition equipment.

The EEG electrode array circuit 200, and other circuits, device, and systems described herein, may at least partially mitigate one or more of these problems by reducing the wire count between the electrode array and an external signal acquisition system, and further reducing the extent of the external acquisition system, thus enabling massive scaling of the quantity of contact points without a corresponding increase in the number of wires or leads running between the electrode array circuit 200 and external acquisition system.

Referring to FIG. 2, the EEG electrode array circuit 200 includes multiple sub-circuits 202 arranged in rows and columns. Each sub-circuit 202 corresponds to a different electrode contact (e.g., metal disc). The EEG electrode array circuit 200 includes circuitry for a multiplexer 210 to aggregate signals onto a common wire. As described herein, the intelligent multiplexer 210 can improve performance in multiple ways.

In general, a multiplexer is a circuit that accepts analog signals from multiple sources and combines them in an aggregated signal. The signals are combined in a manner that allows the individual input signals to be recovered by a de-multiplexer. For example, in a time-division scheme, the multiplexer may allow just one input signal to pass through to the output at a time. In effect, such a multiplexer acts as a single pole, multi-throw switch. The multiplexer 210 can be an intelligent multiplexer (iMux), which can be configured to follow one of several specific patterns. For example, the intelligent multiplexer 210 can sample across the top row of electrode contact points, and then subsequently sample the next row of points, and so forth. As an alternative example, the intelligent multiplexer 210 can sample every-Nth contact point to reduce the quantity of samples by a factor of N while effectively sensing across the full area of the electrode array. In an addition example, the intelligent multiplexer 210 can sample the first M rows and 0 columns of contact points to maintain maximum physical resolution in a sub-region of the electrode array. In an alternative implementation, the multiplexer 210 may be a digital multiplexer.

Because sequential sampling across a large number of contact points can introduce meaningful time differentials between the times when electrical activity of the brain is measured at different points, the electrode array circuit 200 can alternatively be configured to sample an electrical characteristic (e.g., a voltage, current, or resistance) of all or a subset of the contact points of the array 200 at substantially the same time (simultaneously).

Referring still to FIG. 2, the EEG electrode array circuit 200 includes a sensor port 220 and a sample/hold circuit 230 in each sub-circuit 202. The electrode's contact points are connected to their respective sensor ports 220. At each sensor port 220, the sample/hold circuit 230 is provided which samples an input signal representing local electrical activity of the brain, and holds the sampled value until reset. In some implementations, to time-align the sampling, a common snapshot signal 250 is distributed to all or some of the sample/hold circuits 230. The snapshot signal 250 activates the sample/hold circuits 230 causing them to sample their respective signals (e.g., by sampling a voltage, resistance, or current value measured by the corresponding electrode contact point for the particular sample/hold circuit 230). The sampled value can be an analog value or digital value. In addition, the snapshot signal 250 can effectively reset the sample/hold circuits 230 during a next snapshot pulse. Through the use of the snapshot signal and corresponding sample/hold circuits, the signals across the entire EEG electrode array circuit 200 can be simultaneously captured.

After the measurements are captured, the intelligent multiplexer 210 sequentially retrieves the sampled values from each of the sample/hold circuits 230 corresponding to each contact point. The selected signal measurement is then forwarded to a signal acquisition system 240. An example of the signal acquisition system 240 includes an analog-to-digital converter (ADC) and a digital signal processor (DSP). The signal acquisition system 240 can be placed external to the patient.

In some implementations, each sub-circuit 202 (e.g., cell) of the array 200 can include local signal-conditioning circuits, such as amplifiers, filters, and integrators, as illustrated in FIG. 2.

As described, a single intelligent multiplexer 210 can service numerous contact points such that all corresponding signals are presented to the external acquisition system 240 through a single wire or wireless link. Further, the array 200 can be scaled up to cover a large array of contact points. By way of example, it is feasible to sample more than 100,000 contacts with the array 200 and aggregate those signals down to a single signal that is transmitted externally from the patient. In addition, the scalability can further increase by providing and grouping multiple intelligent multiplexers together.

In some implementations, the array 200 (e.g., the multiplexer 210) can be connected to the signal acquisition system 240 for a single, common wired transmission. In other implementations, a wireless connection, such as a radio link or optical link, can be used to connect the multiplexer 210 to the signal acquisition system 240.

In addition to reducing the wire count to the external acquisition equipment 240, the array 200 enables simplifying the equipment 240. Instead of having hundreds of connectors, ADCs, and DSPs for respective contact points, the signal acquisition equipment 240 can be reduced to a single connector, single ADC, and single DSP, as illustrated in FIG. 2. Further, the configuration of the array 200, which employs the intelligent multiplexer 210 and the sample/hold circuits 230, can significantly reduce the wire count, thereby also reducing risk to the patient, enabling patient mobility, and enabling massive scaling in the quantity of contact points.

Figure 3:
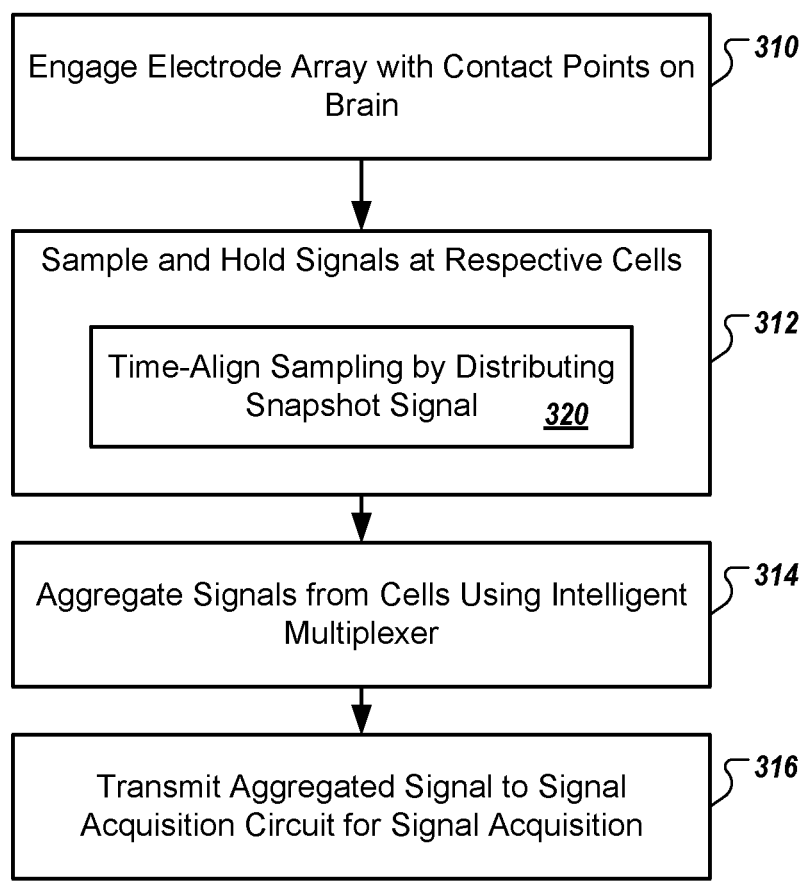
FIG. 3 is a flowchart of an example process for acquiring signals from a brain using an electrode array.

FIG. 3 is a flowchart of an example process 300 for acquiring signals from a brain using an electrode array. For example, the process 300 can be performed using the EEG electrode array circuit 200 of FIG. 2. The process 300 can include engaging an electrode array (e.g., the EEG electrode array circuit 200) with contact points on a brain (Block 310). The process 300 can include sampling and holding input signals at respective cells (e.g., respective sub-circuits 202) (Block 312). In some implementations, the sampling can be time-aligned by distributing a signal (e.g., the snapshot signal 250) throughout all or some of the cells (e.g., the sub-circuits 202) (Block 320). The distributed signal is used to control the respective cells (e.g., the sample/hold circuits 230 therein) to instruct the cells on when to sample their respective input signals (measurements). In some implementations, the distributed signal causes each of the cells to capture their respective measurements at substantially the same time.

The process 300 can include aggregating the signals sampled at the respective cells (Block 314). For example, a multiplexer (e.g., the intelligent multiplexer 210) can be connected to the cells and operated to aggregate the signals from the cells. The process 300 can include transmitting the aggregated signal to a signal acquisition circuit (e.g., the signal acquisition system or equipment 240) which operates to acquire and process the aggregated signal for subsequent use.

EEG Electrode Array with Multi-Resolution Contacts

Typical EEG electrode arrays may be limited in terms of a physical resolution of their contact points. An example of such typical EEG electrode arrays includes an array of contacts placed on a flexible membrane, where the contacts are approximately 1 mm in diameter and placed on a 1 cm pitch. Such a physically-large pitch may be useful in identifying a generalized region of a brain of interest, but the pitch can be too large to pinpoint the location of electrical anomalies for therapeutic purposes.

Some electrode arrays provide finer contact-pitches, which may enable clinicians to pinpoint the location of electrical anomalies for treatment. However, such probes can only cover a relatively-small region of the brain, and thus require prior use of larger-pitch electrodes and/or equipment to identify the general region of interest.

Further, the use of fixed-pitch electrode arrays may limit the accuracy and thus the quality of care. Moreover, fixed-pitch electrode arrays require the use of multiple electrode arrays at the risk of harming the patient from the application/removal/re-application process.

As described herein, some example EEG electrode arrays described herein provide a single electrode array that can adapt its physical resolution from wide pitch (for identifying the general area of interest) to fine pitch (for pinpointing the location for treatment).

An alternative way to gain the most insight into the brain's operation may be to cover the entire brain with contact points that are spaced at the finest-possible spatial resolution. However, there are several technological limits of typical electrode arrays that often preclude such an arrangement (as described above). Further, such an alternative method may not be cost-efficient due in part to complexity of signal acquisition equipment that would be required to acquire and process signals from the electrode array. For example, typical electrodes require each contact point to be individually and independently acquired and, therefore, the cost of the acquisition scales linearly with the quantity of contact points. By way of example, doubling the quantity of contact points approximately doubles the cost of the acquisition equipment. If scaled to cover the entire brain as sub-millimeter spatial resolution, the cost of the acquisition equipment is unaffordable. Another practical limitation of using the alternative method relates to ability to process and use all the data. Even if a user could afford such complex acquisition equipment, the amount of data available from such a full-scale electrode array may be beyond the processing capability of commodity computers.

Some implementations of EEG electrode arrays described herein can provide a multi-resolution array, without imposing any of the potential limitations described above. For example, such EEG electrode arrays include a coarse-resolution array that can cover the entire, or a large part of, a brain, and enable clinicians to identify a general area within the brain where an interesting activity is occurring. The coarse resolution can enable extensive or full spatial coverage of the brain while limiting the complexity/cost of the associated acquisition equipment and data-processing computer.

After the general area-of-interest of the brain is identified, the EEG electrode array 400 can change the spatial resolution to a much finer pitch. While doing so, the quantity of contact points can be held constant, thus the effective bandwidth of data to be acquired and processed can be held constant, thus making the overall system affordable and obtainable.

Referring to FIG. 4, an example EEG electrode array 400 is configured and operated similarly to the EEG electrode array circuit 200 above, such as including an intelligent multiplexer 410, sensor ports 420, sample/hold circuits 430, a signal acquisition system 440, a snapshot signal line 450, which are similar to the intelligent multiplexer 210, the sensor ports 220, the sample/hold circuits 230, the signal acquisition system 240, and the snapshot signal line 250, respectively. In addition, the EEG electrode array 400 is configured to provide multi-resolution arrays. For example, the array 400 is configured to aggregate the signals into "groupings" of contact points using adders. The size and shape of the localized regions can be modified to meet a particular need, but regardless the circuit is configured to sum and/or average the signals from multiple contact points to generate an aggregated measurement/signal, and present the aggregate measurement/signal to the user.

As a descriptive example, the EEG electrode array 400 can include contact points on a very-fine 0.1 mm pitch, thus enabling 0.1 mm spatial resolution. Each contact point could be connected to the intelligent multiplexer (iMux) 410, thus enabling each and every contact point to be independently sampled. In addition, each contact point within a certain region of the array (e.g., 10×10 sub-array) can be connected to a local adder circuit 460, where all the collection of 100 signals are summed/averaged, and the aggregate signal is connected to the iMux 410. Through proper control of the iMux 410, the user can then be presented with the signals from each individual contact point when fine spatial resolution (e.g., 0.1 mm) is needed, or the user could be presented with just the aggregate signals when course spatial resolution (e.g., 1 mm) is better suited.

As such, the EEG electrode array 400 can provide additional benefits. For example, by summing the voltages from across the contact points, the resulting signal will suppress the noise simply through mathematical averaging of the contact points. Further, the effective contact resistance between the contacts and the brain can be reduced due to the parallel connections of the multiple contacts. These benefits can further improve the resulting signal quality.

FIG. 5 is a flowchart of an example process 500 for acquiring signals from a brain using an electrode array. For example, the process 500 can be performed using the EEG electrode array 400 of FIG. 4. The process 500 can include engaging an electrode array (e.g., the EEG electrode array 400) with contact points in a brain (Block 510). The process 500 can include sampling and holding input signals at respective cells (e.g., respective sub-circuits 402) (Block 512). In some implementations, the sampling can be time-aligned by distributing a signal (e.g., the snapshot signal 450) throughout all or some of the cells (e.g., the sub-circuits 402) (Block 520). The distributed signal is used to control the respective cells (e.g., the sample/hold circuits 430 therein) to instruct the cells on when to sample their respective input signals.

In some implementations, the cells (e.g., the sub-circuits 402) that correspond to respective contact points can be grouped to cover larger regions (e.g., cell groups 404 in FIG. 4) which correspond to respective groups of cells or contact points. The process 500 can include aggregating signals from respective groups of cells (Block 514). For example, for each cell group 404, the signals from the respective cells are aggregated (e.g., collected, summed, averaged, etc.) to generate a first aggregate signal.

The process 500 can include aggregating the first aggregate signals from the respective cell groups to generate a second aggregate signal (Block 516). For example, a multiplexer (e.g., the intelligent multiplexer 410) can be connected to the cell groups and operated to aggregate the first aggregate signals from the cell groups. The process 500 can include transmitting the second aggregate signal to a signal acquisition circuit (e.g., the signal acquisition system or equipment 440) which operates to acquire and process the signal for subsequent use.

Referring to FIG. 6, an example structure of an EEG electrode array membrane 600 is illustrated for providing multi-resolution contact points. The EEG electrode array membrane 600. FIG. 6 illustrates a zoomed-in view of contact points 670 (including 680 and 690) on the surface 672 of the electrode array membrane 600. A plurality of fine-resolution contact points 680 are distributed in a regular array across the surface 672 of the electrode array membrane 600. In addition, the electrode array membrane 600 includes perforated plates 690 surrounding the fine-resolution contact points 680. For example, each plate 690 includes a plurality of holes 692, and the fine-resolution contact points 680 are disposed within the respective holes 692. The plates 690 can act as coarse-resolution contact points themselves. As the shapes of the plates 690 are physically larger, they can provide larger spatial resolution and better contact resistance. All contact points—including the discrete/small ones (i.e., the fine-resolution contact points 680) and the larger ones (i.e., the coarse-resolution contact points 690)— are presented to an intelligent multiplexer (similar to the iMux 210 or 410), and thus they can be selected as needed to obtain a measurement for selectively larger or smaller areas of the brain.

As such, the array circuit 400 and array membrane 600 can provide multiple spatial resolutions within a single electrode array, thereby reducing risk to the patient, expediting diagnoses and treatment, and improving accuracy of treatment.

EEG Electrode Array with Simultaneous Sense and Stimulation

Typical EEG electrode arrays are limited to sensing (acquiring) signals from the brain, and cannot be used for stimulating or treatment of the brain. In practice, EEG electrode arrays are first placed on the scalp or brain to diagnose the ailment and pinpoint the tissue of interest. The electrode array and associated equipment are then physically removed from the patient. Separate equipment is then brought in to treat the tissue, after which the stimulation equipment is removed, and the EEG electrode array is often then re-applied to measure the effectiveness of the treatment. The act of removing and re-applying electrodes poses risk to the patient. It also constrains treatment to open-loop techniques, which degrades accuracy and effectiveness of the treatment.

Some implementations of EEG electrode arrays described herein are configured to provide treatment therapies through electrical stimulation (e.g., electroconvulsive therapy, vagus nerve stimulation [VNS], and deep brain stimulation [DBS]) while simultaneously sensing the brain's activities.

Figure 7:
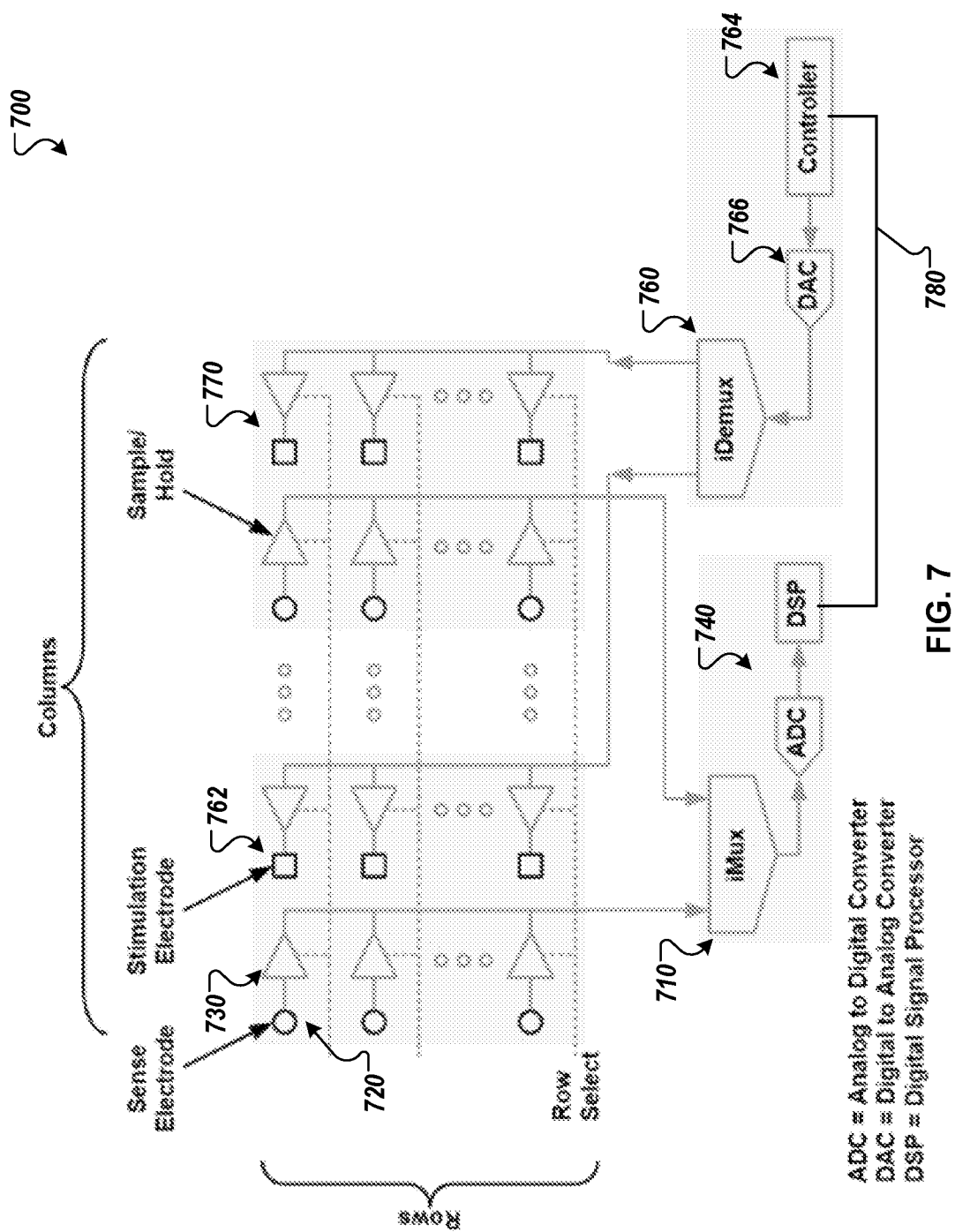
FIG. 7 illustrates a diagram of an example EEG electrode array circuit for enabling sensing and stimulation through the same electrode array.

FIG. 7 illustrates a diagram of an example EEG electrode array circuit 700 for enabling sensing and stimulation through the same electrode array. The EEG electrode array circuit 700 may be configured similarly to the array circuits 200, 400. For example, the EEG electrode array circuit 700 includes sensing circuitry similar to at least part of the array circuits 200, 400, such as including an intelligent multiplexer 710, sensor ports 720, sample/hold circuits 730, a signal acquisition system 740, a snapshot signal line, which are similar to the intelligent multiplexer 210, 410, the sensor ports 220, 420, the sample/hold circuits 230, 430, the signal acquisition system 240, 440, and the snapshot signal line 250, 450, respectively.

In addition to (or in parallel with) the sensing circuitry, the EEG electrode array circuit 700 includes an intelligent demultiplexer (iDemux) 760 configured to inject electrical signals into the contact points (through stimulation electrodes 762). In the illustrated example, the sensing and stimulating contact points are configured as separate entities. However, in other examples, the electrical circuit can be designed to enable common contact points to be shared for both sensing and stimulating. The EEG electrode array circuit 700 can further include a controller 764 for controlling the demultiplexer 760. The controller 764 may be connected to the demultiplexer 760 via other signal conditioning elements, such as a digital-to-analog converter 766 (DAC) to produce an analog signal that is further modified by signal-conditioning circuits 770, such as amplifiers, filters, and integrators, as illustrated in FIG. 7.

In one embodiment of the EEG electrode array circuit 700, the sensing circuits (including 730, 710, 740) are actively sensing the patient while the stimulation circuits (including 770, 760, 766, 764) are inactive. By doing so, the stimulation circuits (including 770, 760, 766, 764) are not inadvertently creating EM signals that are couple into the brain or the sensing circuits (including 730, 710, 740), thus improving the quality of the sensed signals.

Alternatively, the EEG electrode array circuit 700 can be configured to inactivate the sensing circuits (including 730, 710, 740) and activate stimulation circuits (including 770, 760, 766, 764) to stimulate the patient's brain. In this configuration, the stimulated signals are applied to the patient.

Also, the EEG electrode array circuit 700 can be configured to simultaneously activate both the sensing circuits (including 730, 710, 740) and stimulation circuits (including 770, 760, 766, 764). In this configuration, the sensing circuits (including 730, 710, 740) can be used to either: 1) measure the applied signals from the stimulation circuits (including 770, 760, 766, 764); or 2) measure the patient's response to the applied signals. Of particular interest, applying a feedback path 780 between the signal acquisition system 740 and the controller 764, the sensed signal can be used to calibrate and adjust the strength and characteristics of the stimulation signal, thus improving clinical effectiveness and reducing risk to the patient.

While the EEG electrode array circuit 700 is generating stimulation signals, the intelligent demultiplexer 760 enables a wide range of options, such as: 1) it can send the same signal to all contact points 762, thus stimulating large sections of the brain; 2) it can selectively send the same signal to a user-defined subset of contact points 762, thus stimulating smaller sections of the brain; 3) it can selectively send different signals to each contact point 762, thus effectively stimulating the brain with a three-dimensional waveform (X, Y, and time); or 4) it can send a signal to a user-selected single contact point 762, thus enabling precise application of stimulation signals.

Figure 8:
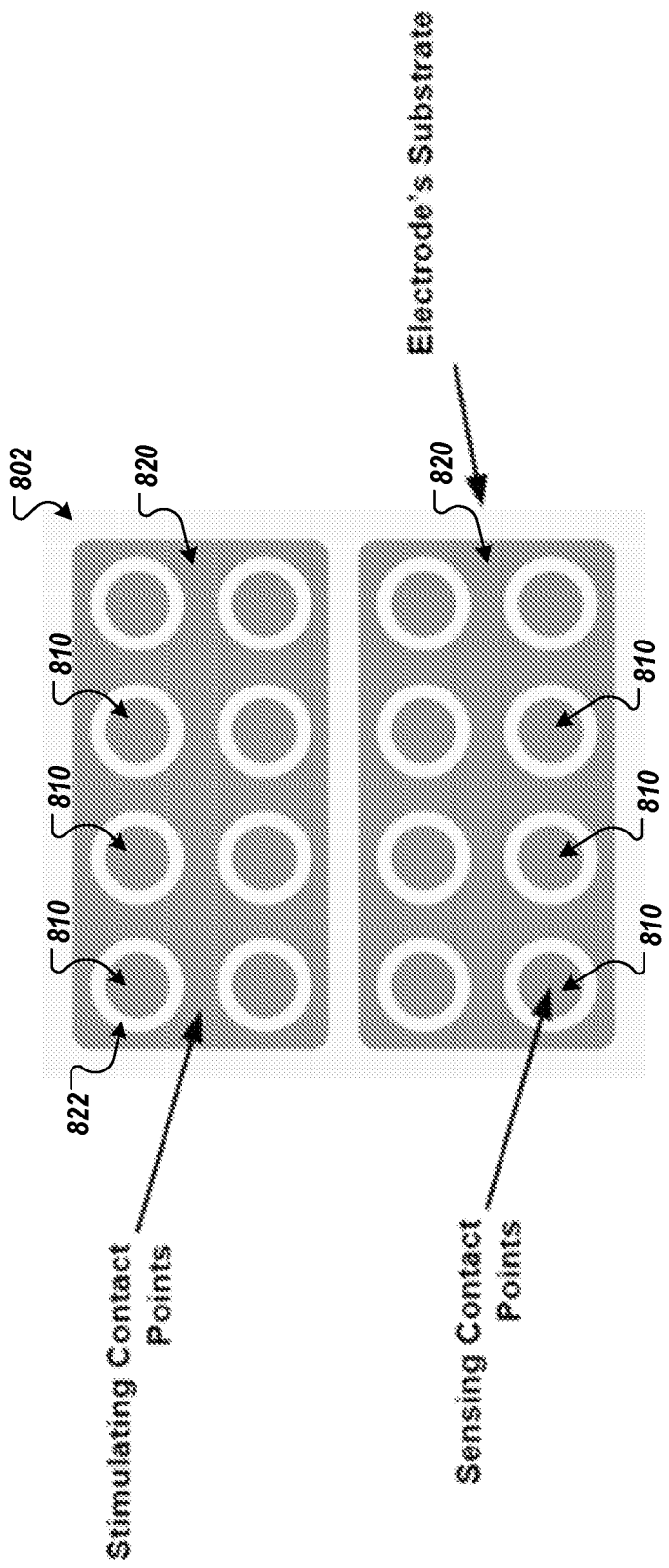
FIG. 8 illustrates an example structure of an EEG electrode array membrane for enabling simultaneous sensing and stimulating.

Referring to FIG. 8, an example structure of an EEG electrode array membrane 800 is illustrated for enabling simultaneous sensing and stimulating. The array membrane 800 is configured to leverage the example structure of the array 600 as depicted in FIG. 6. The array membrane 800 includes a substrate 802 that includes sensing contact points 810 and stimulating contact points 820 which are electrically isolated from one another. For example, the sensing contact points 810 are interspersed within the stimulating contact points 820. Each stimulating contact point 820 can include a plurality of holes 822, and the sensing contact points 810 are disposed within the respective holes 822. In this particular example, the stimulating contact points 820 are physically larger and surrounding the sensing contact points 810, but other configurations can be designed.

As such, the array circuit 700 and membrane 800 provides the ability to sense and stimulate signals with one electrode array, thereby reducing risk to the patient simply due to the elimination of need to apply/remove/reapply electrodes for the different purposes. In addition, the array circuit 700 and membrane 800 can further provide the ability to perform real-time, closed-loop treatment to patients. That is, the patient's condition can be continually monitored (sensed) during treatment (stimulated), which enables more precise and safer treatment.

Figure 9:
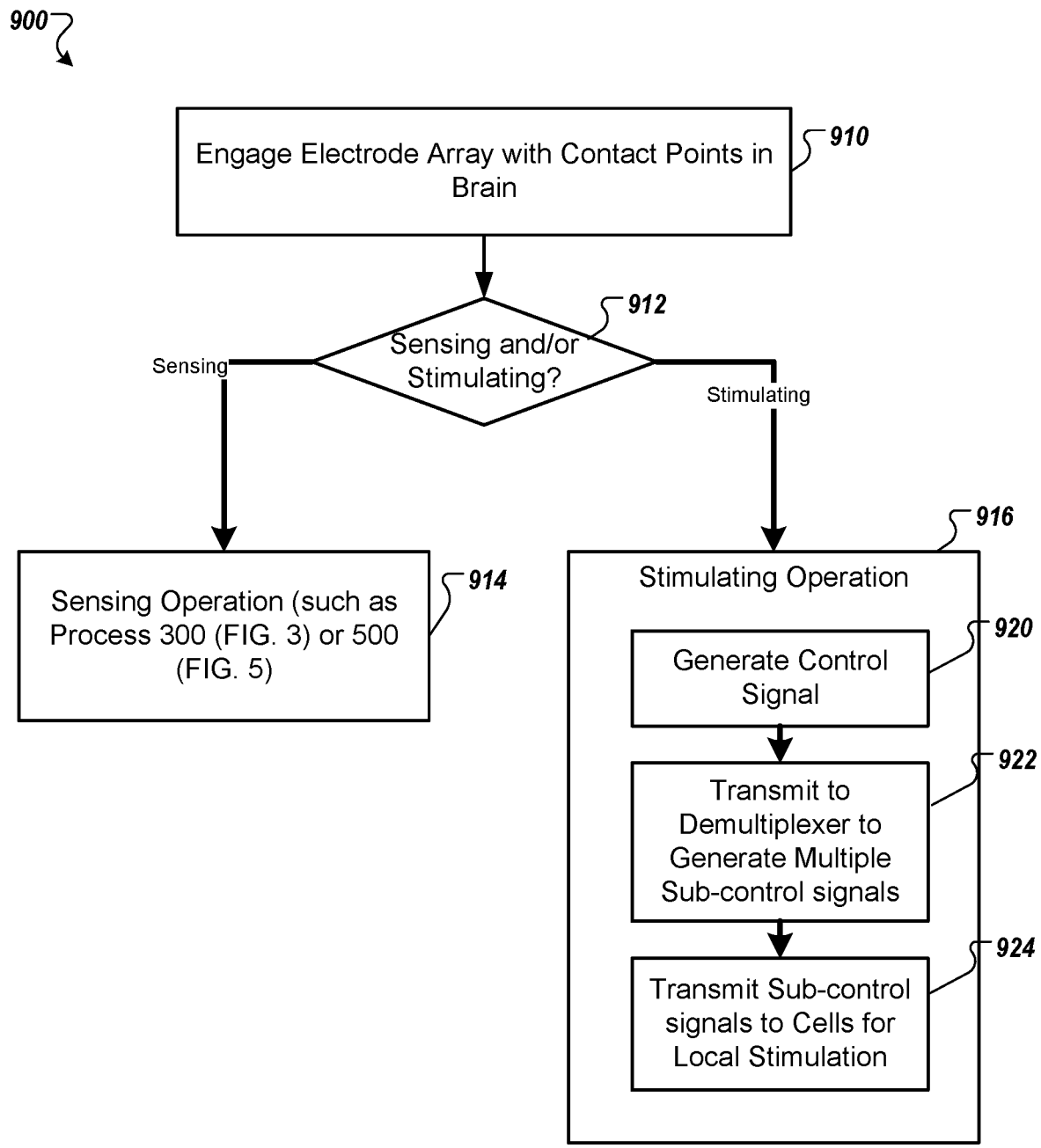
FIG. 9 is a flowchart of an example process for sensing and stimulating a brain using an electrode array.

FIG. 9 is a flowchart of an example process 900 for sensing and stimulating a brain using an electrode array. For example, the process 900 can be performed using the EEG electrode array circuit 700 and membrane 800 of FIGS. 7 and 8. The process 900 can include engaging an electrode array (e.g., the EEG electrode array circuit 700, 800) with contact points in a brain (Block 910). The process 900 can include determining whether the electrode array is in a sensing mode or a stimulating mode (Block 912). If it is in a sensing mode, the process continues on by performing a sensing operation (Block 914). Example sensing operations can be described as the processes 300 (FIG. 3) and 500 (FIG. 5). Other processes are also possible for the sensing operation.

If the electrode array is determined to be in a stimulating operation, the process includes a stimulating operation (Block 916). For example, the stimulating operation can be performed by generating a control signal (Block 920), transmitting the control signal to a demultiplexer (e.g., the intelligent demultiplexer described herein) to generate multiple sub-control signals (Block 922), and transmitting the sub-control signals to the cells for local stimulation (Block 924).

EEG Electrode Array with Conforming Shape

Electrode arrays may be typically fabricated in simple rectangular patterns on flexible, non-elastic membranes. The flexibility enables the electrode to conform in one dimension of the brain's curvature, but it limits the conformity in the other direction. By analogy, a common sheet of paper can be rolled in one direction, but if that same sheet of paper is forced to conform to the shape of a sphere (e.g., ball), the paper will crinkle and crease around the periphery. Such crinkles and creases in electrode arrays pose potential harm to the patient, and they separate the contact points from the brain, thus rendering those particular contacts useless.

Some implementations of EEG electrode arrays described herein are configured to conform to spherical-like objects, such as the brain, while maintaining consistent contact pressure without creating crinkles and creases. Further, the arrays are modular, enabling clinicians to create custom sized and shaped arrays based on the pattern of patches selected and applied.

Figure 10:
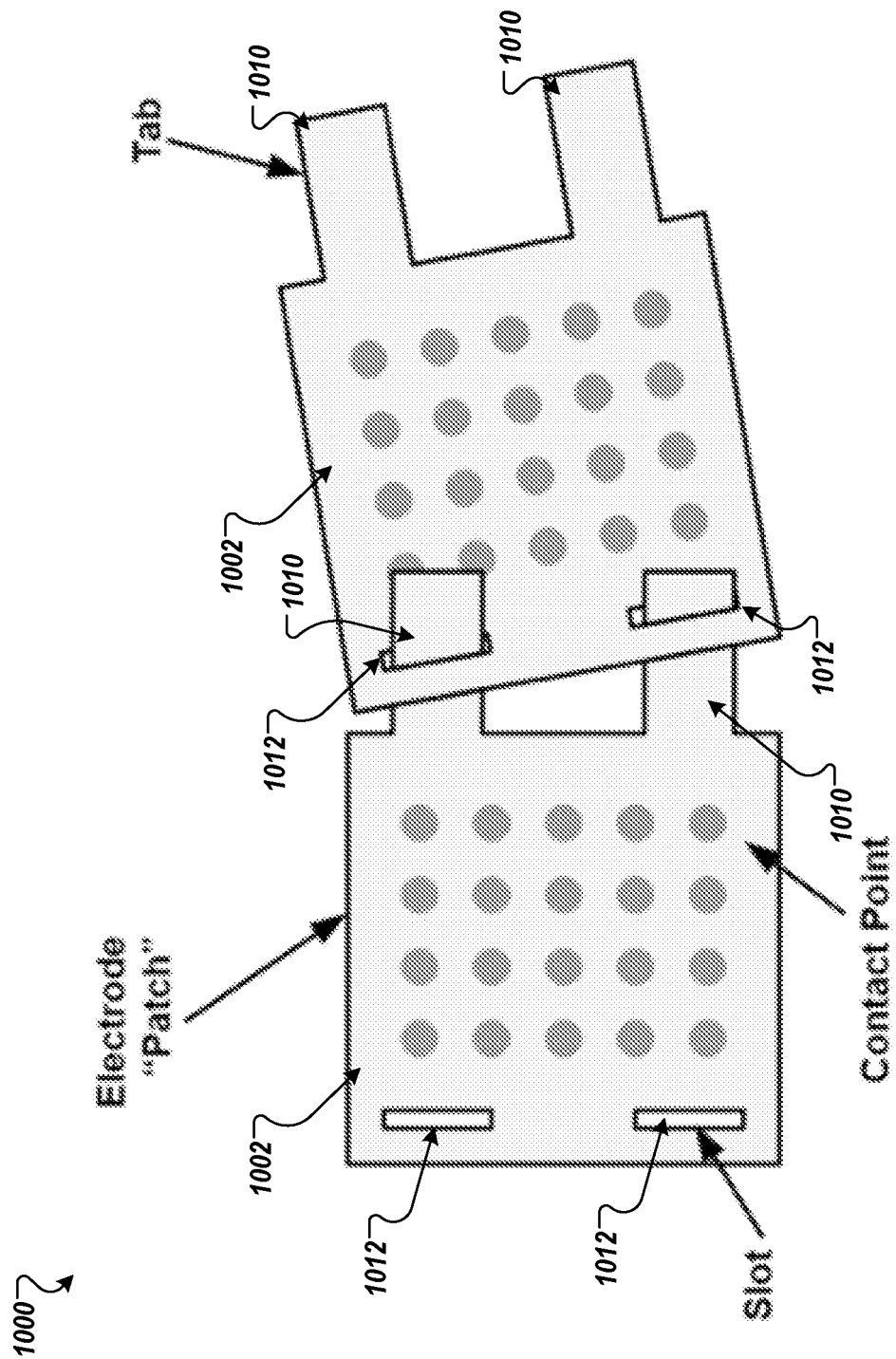
FIG. 10 illustrates an example EEG electrode array membrane constructed with a plurality of patches to provide consistent and sufficient contact pressure across all contact points.

Referring to FIG. 10, an example EEG electrode array membrane 1000 can be constructed with a plurality of patches 1002 to provide consistent and sufficient contact pressure across all contact points. The EEG electrode array membrane 1000 can be configured similarly to the arrays 200, 400, 700, for example. Two patches are depicted in FIG. 10, but more than two patches can be envisioned. In some implementations, each patch 1002 has one or more tabs 1010 at an end, and one or more slots 1012 at an opposite end. The tabs 1010 from one patch 1002 can be inserted through the slots 1012 of an adjoining patch 1002. Although each patch 1002 is illustrated to have two tabs on one side of a square patch, but different shaped patches, quantity and placement of tabs, and quantity and placement of slots are envisioned to enable a wide range of configurations.

The EEG electrode array membrane 1000 with patches can provide several advantageous configurations. For example, the array membrane 1000 can have graduated scales on them, thus enabling the physician to precisely record the relative insertion of each patch. With this information, the physician can numerically determine the shape of the overall array and can later replicate the placement and position of the patches.

Further, by recording the insertion of each tab, the physician can precisely recreate the same aggregate shape and pattern of the electrode array. That is, the insertion lengths of each tab will enable physicians to create a computer aided design (CAD) model of the three-dimensional (3D) shape of the overall electrode array and thus of the brain's outer surface.

The tabs enable the patches to be bonded to one another. With the use of adhesives or fasteners, the tabs from one patch can be held in constant position on the adjacent patch. By doing, the relative position of the overall electrode array will remain constant.

Correspondingly, the overall electrode array can be physically removed from the patient, all the while the overall electrode array retaining its geometrical shape. If needed, the tabs then allow the electrode array to be reapplied to the patient in the precise location where it was originally placed. Finally, the tabs can also provide electrical connectivity between patches. As discussed a bit later, providing electrical connectivity between patches will improve signal quality/fidelity.

The tabs can provide a convenient location to place the electronics, such as the iMux described earlier. In particular, a tab with the iMux could be bent outward from the brain, thus thermally isolating the heat generated by the iMux from harming the brain.

Similarly, the same or different tab can be used to connect to the external acquisition equipment or host the iDemux.

To further aid in generating a 3D CAD model of the array, the tabs and/or the patch itself can have identifying marks on them. For example, each tab can have a fiducial that identifies the physical location of that tab. Using Xray, CT, MR, visual, or other imaging techniques, the 3D location of the fiducials can be precisely identified and recorded.

Moreover, the patches enable a broad range of scalability. A single patch can be used to cover a small, specific area of the brain. Or, a collection of patches can be applied to cover the entire brain. In patch form, there's no inherent limit to the quantity of patches or the physical area which they cover.

In the illustrated embodiment in FIG. 10, the patches are configured as being discrete from one another. In other embodiments, all or some patches can be provided on a common substrate. In such embodiments (not shown), the tabs are at fixed locations on the patches, and they inter-stitch between the patches. To conform to the brain's shape, the tabs are bent upward and crimped to shorten the physical distance between the patches, thus producing the same effect.

As described above, through the use of patches with tabs, the electrode array can conform to the brain's three-dimensional shape without degradation of contact resistance or harm to the patient.

EEG Electrode Array with Ground Reference

Typical EEG electrode arrays are configured to separate the "ground" contact from the other contacts. That is, the primary signals are acquired from contact points that are placed across the brain, and a separate contact point (i.e., most often with a large, single contact point) is located on a physically-separate location of the brain. This separate single-contact electrode is designated as "ground," and it is used as a voltage reference for all the other signals.

The physical separation of the ground contact degrades the quality of the detected signals. In brief, physical separation of the wires creates an electromagnetic (EM) environment that is susceptible to external EM noise. The external noise is generated from man-made emitters such as cell phones, fluorescent lighting, radio towers, and surrounding surgical equipment. And nature creates EM noise through variations in the earth's magnetic fields.

The EM noise manifests itself in two general forms: common mode and differential mode. Common-mode noise has the effect of offsetting all signals by the same voltage amount relative to the "ground" contact. Differential-mode noise has the effect of offsetting the signals relative to one another. Common- and differential-mode noise cannot be completely shielded; it will affect the quality of all signals. However, typical methods of separating the ground contact increase the susceptibility to external noise and thus degrades performance.

Some implementations of EEG electrode arrays described herein provide a physical design that reduces the susceptibility to external EM noise.

As described above, electrode arrays are susceptible to EM noise. Such EM noise comes from nature, man-made sources, and from themselves (i.e., crosstalk). The susceptibility to noise is directly dependent on the relative separation between the electrode's "signal" contacts and the "ground" contact.

Figure 11B:
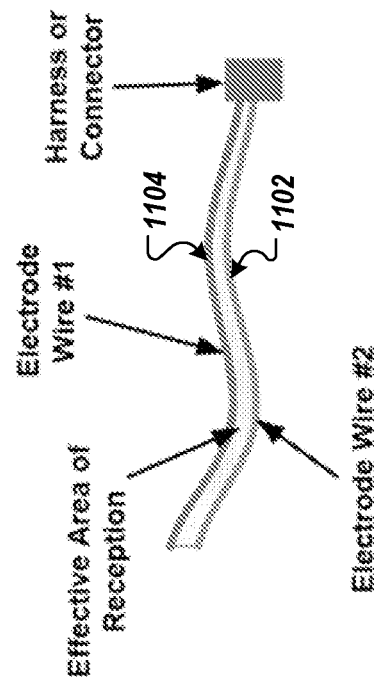
FIG. 11B illustrates an example configuration of electrodes for reducing noise susceptibility in EEG electrodes.
Figure 11A:
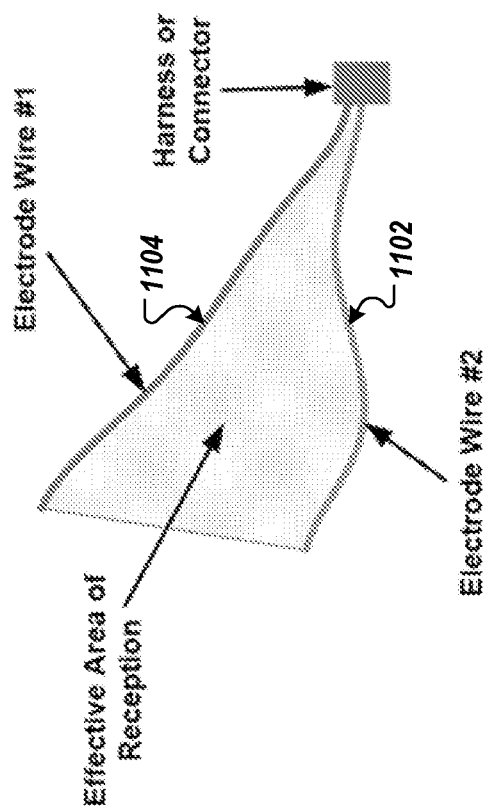
FIG. 11A illustrates an example configuration of electrodes that are highly susceptible to EM noise.

Referring to FIG. 11A, an example configuration 1100A of electrodes is illustrated, which are highly susceptible to EM noise. For example, a first electrode wire 1102 is designated as the "ground" contact or wire, and a second wire 1104 is designated as the "signal" contact or wire. Based on classical antenna theory, the amount of signal that an antenna receives is directly proportional to its aperture, and its aperture is approximated by the effective physical area between signal and ground wires. In the case of EEG electrodes, the reception is of EM noise, so the larger the area (i.e., larger the aperture) increases the electrode's susceptibility to noise. As previously discussed, the ground electrode is often placed on the opposite side of the brain relative to the signal electrodes, which creates the largest-possible aperture and thus maximizes the noise susceptibility.

Referring to FIG. 11B, an example configuration 1100B of electrodes is illustrated for reducing noise susceptibility in EEG electrodes. For example, the electrode configuration 1100B is to reduce the aperture by reducing the separation between the signal wire 1104 and the ground wire 1102. In some implementations, the signal wire 1104 is at least partially routed substantially parallel with the ground wire 1102. The signal wire 1104 can be spaced apart from the ground wire 1102 at a distance ranging between 1 micron and 10 mm.

An approach of pairing each signal wire with a ground wire may double the wire count and the quantity of contact points. Further, by placing grounds across the brain's entire surface, the electrical signals may effectively be shorted to one another, thus masking the signals from detection. Moreover, the ground wires themselves act as antennas, and the existence of numerous ground wires can inadvertently increase noise due the common-mode noise received through the grounds.

The configuration 1100B of electrodes, which minimizes the aperture, can use one common ground across the entire electrode array, where the sole ground contact is placed near the furthest distance away from the external acquisition equipment. In some implementations, the ground "wire" can be implemented as a planar sheet of metal, called a ground plane. The ground plane needs to be continuous across all or part of the electrode array substrate, or of all the patches as shown in FIG. 10 where the tabs provide connectivity between the patches. The ground plane can be placed immediately underneath each and every signal trace.

To provide the singular ground contact to the brain, a contact point within a standard electrode array can be used. In alternative embodiments, a custom electrode can be made that has a large, singular contact point.

As described above, through the use of ground planes within and between patches (as shown in FIG. 10), the electrode can be significantly immune to external EM noise, thus improving the quality of electrical signal and patient care.

Example Embodiments A—Electrode Circuit with Intelligent Multiplexer and Sample/Hold A1. A brain electrode device comprising:
  a plurality of contact points;
  a plurality of sub-circuits including sensor ports configured to connect to the contact points, respectively; and
  an intelligent multiplexer configured to aggregate signals from the plurality of sub-circuits and generate an aggregate signal, wherein the aggregate signal is transmitted to a signal acquisition device.
A2. The brain electrode device of embodiment A1, wherein the plurality of sub-circuits includes sample/hold circuits configured to sample respective input signals and hold its value.
A3. The brain electrode device of embodiment A2, further comprising:
  a snapshot signal circuit configured to instruct the sample/hold circuits with timings of sampling the input signals.
A4. The brain electrode device of embodiment A3, wherein the snapshot signal is configured to reset the sample/hold circuits during a next snapshot pulse.
A5. The brain electrode device of any one of embodiments A1-A4, wherein the signal acquisition system includes an analog-to-digital converter and a digital signal processor.
A6. A method for sensing signals from a brain, comprising:
  engaging an electrode array with the brain, the electrode array including a plurality of cells;
  sampling signals at the respective cells;
  aggregating, using an intelligent multiplexer, the signals; and
  transmitting an aggregated signal to a signal acquisition circuit for processing.
A7. The method of embodiment A6, further comprising:
  holding the signals at the respective cells.
A8. The method of any one of embodiments A6-A7, further comprising:
  time-aligning the signals prior to aggregating the signals.
A9. The method of embodiment A7, wherein time-aligning the signals comprises:
  injecting a snapshot signal to the cells, the snapshot signal configured to control timings of sampling the signals at the respective cells.

Example Embodiment B—Electrode Circuit with Intelligent Demultiplexer

B1. A brain electrode device comprising:
  a plurality of contact points;
  a plurality of sub-circuits including sensor ports configured to connect to the contact points, respectively; and
  an intelligent demultiplexer configured to accept an input signal an aggregate of signals from a control device, the input signal being an aggregate of signals, the intelligent demultiplexer configured to distribute the signals in the input signal to their respective destinations.

Example Embodiments C—Electrode Array with Multi-Resolution Contacts

C1. A brain electrode device comprising:
  a plurality of contact points;
  a plurality of sub-circuits including sensor ports configured to connect to the contact points, respectively; and
  a plurality of adder circuits, each adder circuit configured to aggregate signals from a group of sub-circuits and generate an adder aggregate signal, the group being selected from the plurality of sub-circuits; and
  an intelligent multiplexer configured to aggregate signals directly from the plurality of sub-circuits, or aggregate the adder aggregate signals from the adder circuits, the intelligent multiplexer configured to generate an aggregate signal being transmitted to a signal acquisition device.
C2. The brain electrode device of embodiment C1, wherein the plurality of sub-circuits includes sample/hold circuits configured to sample respective input signals and hold its value.
C3. The brain electrode device of embodiment C2, further comprising:
  a snapshot signal circuit configured to instruct the sample/hold circuits with timings of sampling the input signals.
C4. The brain electrode device of embodiment C3, wherein the snapshot signal is configured to reset the sample/hold circuits during a next snapshot pulse.
C5. The brain electrode device of any one of embodiments C1-C4, wherein the signal acquisition system includes an analog-to-digital converter and a digital signal processor.
C6. A method for sensing signals from a brain, comprising:
  engaging an electrode array with the brain, the electrode array including a plurality of cells and groups of cells being selected from the plurality of cells;
  sampling signals at the respective cells;
  aggregating, using each of a plurality of adder circuits, signals from each of the groups of cells to generate a first aggregate signal;
  aggregating, using an intelligent multiplexer, the first aggregate signals from the plurality of adder circuits to generate a second aggregate signal; and
  transmitting the second aggregate signal to a signal acquisition circuit for processing.

C7. The method of embodiment C6, further comprising:
aggregating, using the intelligent multiplexer, the signals from the cells; and
transmitting the aggregated signal to the signal acquisition circuit.

C8. The method of any one of embodiments C6-C7, further comprising:
holding the signals at the respective cells.

C9. The method of any one of embodiments C6-C8, further comprising:
time-aligning the signals prior to aggregating the signals.

C10. The method of embodiment C7, wherein time-aligning the signals comprises:
injecting a snapshot signal to the cells, the snapshot signal configured to control timings of sampling the signals at the respective cells.

C11. A brain electrode device comprising:
an electrode array membrane;
a plurality of fine-resolution contact points distributed in an array across a surface of the electrode array membrane; and
a coarse-resolution contact point including a perforated plate, the plate having a plurality of holes within which the plurality of fine-resolution contact points are disposed.

Example Embodiments D—Electrode Array with Simultaneous Sense and Stimulation

D1. A brain electrode device comprising:
a sensing circuit including:
a plurality of first contact points;
a plurality of first sub-circuits including sensor ports configured to connect to the first contact points, respectively; and
an intelligent multiplexer configured to aggregate signals from the plurality of first sub-circuits and generate an aggregate signal, wherein the aggregate signal is transmitted to a signal acquisition device; and
a stimulating circuit including:
a plurality of second contact points;
a plurality of second sub-circuits including sensor ports configured to connect to the second contact points, respectively; and
an intelligent demultiplexer configured to receive a single stimulation signal from a controller and generate a plurality of sub-stimulation signals being transmitted to the plurality of second sub-circuits.

D2. The brain electrode device of embodiment D1, wherein the sensing and the stimulating circuit are operated independently.

D3. The brain electrode device of any one of embodiments D1-D2, wherein the sensing circuit and the simulating circuit are simultaneously operated.

D4. The brain electrode device of any one of embodiments D1-D3, wherein the plurality of sub-circuits includes sample/hold circuits configured to sample an input signal and hold its value.

D5. The brain electrode device of embodiment D4, further comprising:
a snapshot signal circuit configured to transmit a snapshot signal to instruct the sample/hold circuits with timings of sampling the input signals.

D6. The brain electrode device of embodiment D5, wherein the snapshot signal is configured to reset the sample/hold circuits during a next snapshot pulse.

D7. The brain electrode device of any one of embodiments D1-D6, wherein the signal acquisition system includes an analog-to-digital converter and a digital signal processor.

D8. A method for sensing signals from a brain and stimulating the brain, comprising:
engaging an electrode array with the brain, the electrode array including a plurality of cells;
sensing signals from the brain by:
sampling signals at the respective cells;
aggregating, using an intelligent multiplexer, the signals; and
transmitting an aggregated signal to a signal acquisition circuit for processing; and
stimulating the brain by:
obtaining a stimulation signal;
generating, using an intelligent demultiplexer, a plurality of sub-stimulation signals from the stimulation signal; and
transmitting the plurality of sub-stimulation signals to the plurality of cells.

D9. The method of embodiment D8, wherein sensing the signals from the brain is performed simultaneously with stimulating the brain.

D10. The method of any one of embodiments D8-D9, wherein sensing the signals from the brain further comprises:
holding the signals at the respective cells.

D11. The method of any one of embodiments D8-D10, wherein sensing the signals from the brain further comprises time-aligning the signals prior to aggregating the signals.

D12. The method of embodiment D11, wherein time-aligning the signals comprises:
injecting a snapshot signal to the cells, the snapshot signal configured to control timings of sampling the signals at the respective cells.

Example Embodiments E—Electrode Array with Conforming Shape

E1. A brain electrode device comprising:
a plurality of patches movably connected in array, each patch including:
a plurality of contact points; and
a sub-circuit including a sensor port configured to connect to the contact points; and
an intelligent multiplexer configured to aggregate patch signals from the plurality of contact points into an aggregate signal, wherein the aggregate signal is transmitted to a signal acquisition device.

E2. The brain electrode device of embodiment E1, wherein each patch comprises a tab and a slot configured to receive a tab from an adjoining patch.

E3. The brain electrode device of embodiment E2, wherein each patch comprises a plurality of tabs at an end and a plurality of slots at another end and configured to receive a plurality of tabs from an adjoining patch.

E4. The brain electrode device of embodiment E3, wherein the tabs of the patch are attached to the adjoining patch using adhesive.

E5. The brain electrode device of embodiment E3, wherein the tabs of the patch are attached to the adjoining patch using a fastener.

E6. The brain electrode device of any one of embodiments E1-E5, wherein each path includes:
a patch multiplexer configured to aggregate signals from the sub-circuit in the patch and generate a patch signal.

E7. The brain electrode device of embodiment E3, wherein the tabs are flexible.

E8. The brain electrode device of embodiment E3, wherein the tabs include electronics thereon and are configured to isolate the electronics from a brain tissue to which the plurality of patches is engaged.

E9. The brain electrode device of embodiment E8, wherein the electronics include the intelligent multiplexer.

E10. The brain electrode device of embodiment E3, further comprising:

marks provided on the tabs and configured to measure an effective insertion distance of the tabs.

Example Embodiments F—Electrode Array with Ground Reference

F1. A brain electrode device comprising:
  a plurality of contact points;
  a plurality of sub-circuits including sensor ports configured to connect to the contact points, respectively;
  a ground electrode wire; and
  a signal electrode wire routed parallel with the ground electrode wire and spaced apart from the ground electrode wire at a predetermined distance.

F2. The brain electrode device of embodiment F1, wherein the predetermined distance ranges between 1 micron and 10 millimeters.

F3. The brain electrode device of any one of embodiments F1-F2, further comprising:
  an intelligent multiplexer configured to aggregate signals from the plurality of sub-circuits and generate an aggregate signal, wherein the aggregate signal is transmitted to a signal acquisition device.

F4. The brain electrode device of any one of embodiments F1-F3, wherein the plurality of sub-circuits includes sample/hold circuits configured to sample an input signal and hold its value.

F5. The brain electrode device of embodiment F4, further comprising:
  a snapshot signal circuit configured to transmit a snapshot signal to instruct the sample/hold circuits with timings of sampling the input signals.

F6. The brain electrode device of embodiment F5, wherein the snapshot signal is configured to reset the sample/hold circuits during a next snapshot pulse.

F7. The brain electrode device of any one of embodiments F1-F6, wherein the signal acquisition system includes an analog-to-digital converter and a digital signal processor.

Figure 12:
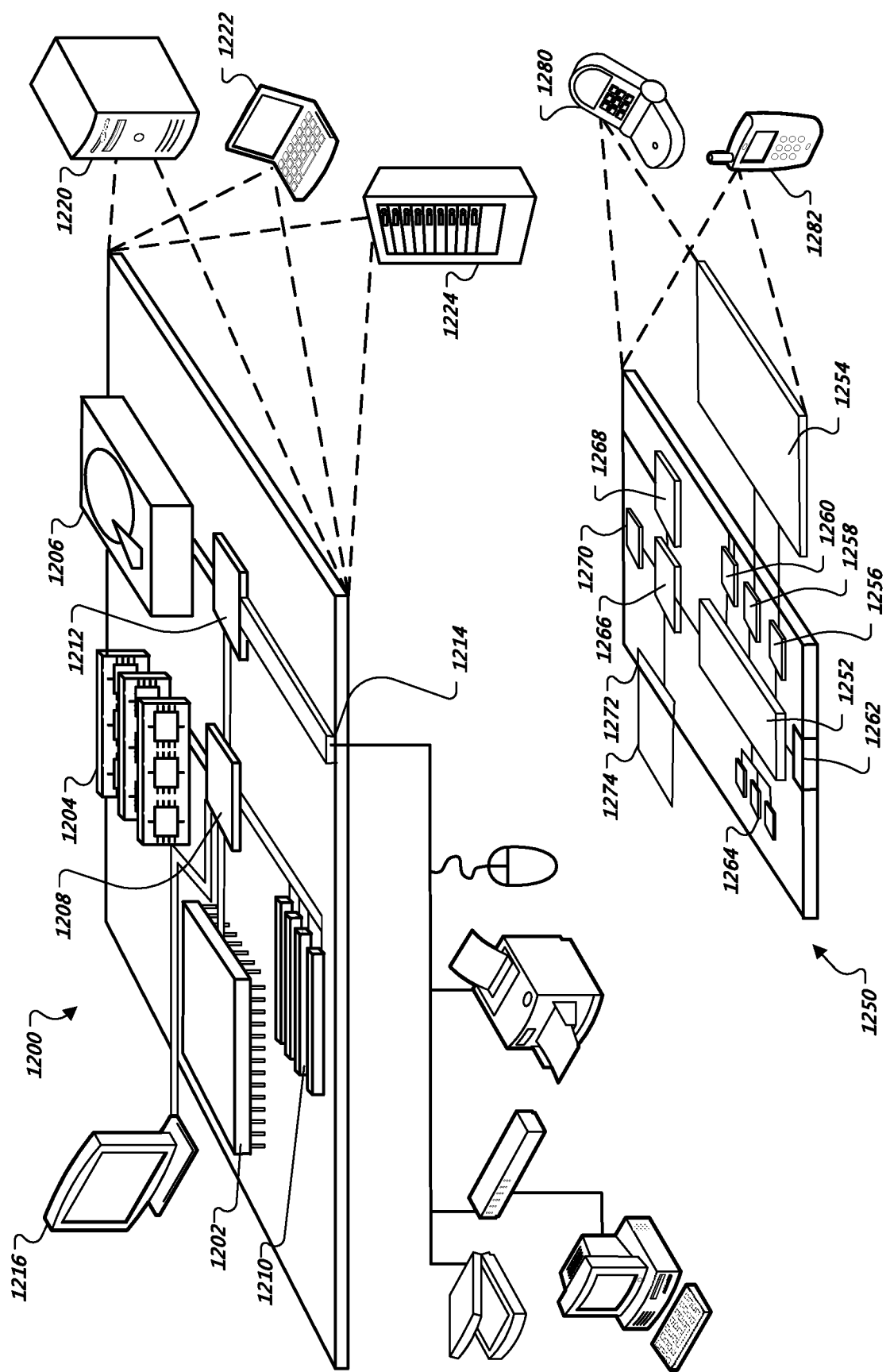
FIG. 12 is a block diagram of computing devices that may be used to implement the systems and methods described in this document.

FIG. 12 is a block diagram of computing devices 1200, 1250 that may be used to implement the systems and methods described in this document, as either a client or as a server or plurality of servers. Computing device 1200 is intended to represent various forms of digital computers, such as laptops, desktops, workstations, personal digital assistants, servers, blade servers, mainframes, and other appropriate computers. Computing device 1250 is intended to represent various forms of mobile devices, such as personal digital assistants, cellular telephones, smartphones, and other similar computing devices. The components shown here, their connections and relationships, and their functions, are meant to be examples only, and are not meant to limit implementations described and/or claimed in this document.

Computing device 1200 includes a processor 1202, memory 1204, a storage device 1206, a high-speed interface 1208 connecting to memory 1204 and high-speed expansion ports 1210, and a low speed interface 1212 connecting to low speed bus 1214 and storage device 1206. Each of the components 1202, 1204, 1206, 1208, 1210, and 1212, are interconnected using various busses, and may be mounted on a common motherboard or in other manners as appropriate. The processor 1202 can process instructions for execution within the computing device 1200, including instructions stored in the memory 1204 or on the storage device 1206 to display graphical information for a GUI on an external input/output device, such as display 1216 coupled to high-speed interface 1208. In other implementations, multiple processors and/or multiple buses may be used, as appropriate, along with multiple memories and types of memory. Also, multiple computing devices 1200 may be connected, with each device providing portions of the necessary operations (e.g., as a server bank, a group of blade servers, or a multi-processor system).

The memory 1204 stores information within the computing device 1200. In one implementation, the memory 1204 is a volatile memory unit or units. In another implementation, the memory 1204 is a non-volatile memory unit or units. The memory 1204 may also be another form of computer-readable medium, such as a magnetic or optical disk.

The storage device 1206 is capable of providing mass storage for the computing device 1200. In one implementation, the storage device 1206 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The information carrier is a computer- or machine-readable medium, such as the memory 1204, the storage device 1206, or memory on processor 1202.

The high-speed controller 1208 manages bandwidth-intensive operations for the computing device 1200, while the low speed controller 1212 manages lower bandwidth-intensive operations. Such allocation of functions is an example only. In one implementation, the high-speed controller 1208 is coupled to memory 1204, display 1216 (e.g., through a graphics processor or accelerator), and to high-speed expansion ports 1210, which may accept various expansion cards (not shown). In the implementation, low-speed controller 1212 is coupled to storage device 1206 and low-speed expansion port 1214. The low-speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 1200 may be implemented in a number of different forms, as shown in the figure. For example, it may be implemented as a standard server 1220, or multiple times in a group of such servers. It may also be implemented as part of a rack server system 1224. In addition, it may be implemented in a personal computer such as a laptop computer 1222. Alternatively, components from computing device 1200 may be combined with other components in a mobile device (not shown), such as device 1250. Each of such devices may contain one or more of computing device 1200, 1250, and an entire system may be made up of multiple computing devices 1200, 1250 communicating with each other.

Computing device 1250 includes a processor 1252, memory 1264, an input/output device such as a display 1254, a communication interface 1266, and a transceiver 1268, among other components. The device 1250 may also be provided with a storage device, such as a microdrive or other device, to provide additional storage. Each of the components 1250, 1252, 1264, 1254, 1266, and 1268, are interconnected using various buses, and several of the components may be mounted on a common motherboard or in other manners as appropriate.

The processor 1252 can execute instructions within the computing device 1250, including instructions stored in the memory 1264. The processor may be implemented as a chipset of chips that include separate and multiple analog and digital processors. Additionally, the processor may be implemented using any of a number of architectures. For example, the processor may be a CISC (Complex Instruction Set Computers) processor, a RISC (Reduced Instruction Set Computer) processor, or a MISC (Minimal Instruction Set Computer) processor. The processor may provide, for example, for coordination of the other components of the device 1250, such as control of user interfaces, applications run by device 1250, and wireless communication by device 1250.

Processor 1252 may communicate with a user through control interface 1258 and display interface 1256 coupled to a display 1254. The display 1254 may be, for example, a TFT (Thin-Film-Transistor Liquid Crystal Display) display or an OLED (Organic Light Emitting Diode) display, or other appropriate display technology. The display interface 1256 may comprise appropriate circuitry for driving the display 1254 to present graphical and other information to a user. The control interface 1258 may receive commands from a user and convert them for submission to the processor 1252. In addition, an external interface 1262 may be provide in communication with processor 1252, so as to enable near area communication of device 1250 with other devices. External interface 1262 may be provided, for example, for wired communication in some implementations, or for wireless communication in other implementations, and multiple interfaces may also be used.

The memory 1264 stores information within the computing device 1250. The memory 1264 can be implemented as one or more of a computer-readable medium or media, a volatile memory unit or units, or a non-volatile memory unit or units. Expansion memory 1274 may also be provided and connected to device 1250 through expansion interface 1272, which may include, for example, a SIMM (Single In Line Memory Module) card interface. Such expansion memory 1274 may provide extra storage space for device 1250, or may also store applications or other information for device 1250. Specifically, expansion memory 1274 may include instructions to carry out or supplement the processes described above, and may include secure information also. Thus, for example, expansion memory 1274 may be provide as a security module for device 1250, and may be programmed with instructions that permit secure use of device 1250. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 1264, expansion memory 1274, or memory on processor 1252 that may be received, for example, over transceiver 1268 or external interface 1262.

Device 1250 may communicate wirelessly through communication interface 1266, which may include digital signal processing circuitry where necessary. Communication interface 1266 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 1268. In addition, short-range communication may occur, such as using a Bluetooth, WiFi, or other such transceiver (not shown). In addition, GPS (Global Positioning System) receiver module 1270 may provide additional navigation- and location-related wireless data to device 1250, which may be used as appropriate by applications running on device 1250.

Device 1250 may also communicate audibly using audio codec 1260, which may receive spoken information from a user and convert it to usable digital information. Audio codec 1260 may likewise generate audible sound for a user, such as through a speaker, e.g., in a handset of device 1250. Such sound may include sound from voice telephone calls, may include recorded sound (e.g., voice messages, music files, etc.) and may also include sound generated by applications operating on device 1250.

The computing device 1250 may be implemented in a number of different forms, as shown in the figure. For example, it may be implemented as a cellular telephone 1280. It may also be implemented as part of a smartphone 1282, personal digital assistant, or other similar mobile device.

Additionally computing device 1200 or 1250 can include Universal Serial Bus (USB) flash drives. The USB flash drives may store operating systems and other applications. The USB flash drives can include input/output components, such as a wireless transmitter or USB connector that may be inserted into a USB port of another computing device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), peer-to-peer networks (having ad-hoc or static members), grid computing infrastructures, and the Internet.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

What is claimed is:

1. A brain electrode device comprising:
    a plurality of contact points;
    a plurality of sub-circuits including sensor ports configured to connect to the contact points, respectively; and
    an intelligent multiplexer configured to aggregate signals from the plurality of sub-circuits and generate an aggregate signal, wherein the aggregate signal is transmitted to a signal acquisition device.

2. The brain electrode device of claim 1, wherein the plurality of sub-circuits includes sample/hold circuits configured to sample respective input signals and hold its value.

3. The brain electrode device of claim 2, further comprising:
    a snapshot signal circuit configured to instruct the sample/hold circuits with timings of sampling the input signals.

4. The brain electrode device of claim 3, wherein the snapshot signal is configured to reset the sample/hold circuits during a next snapshot pulse.

5. The brain electrode device of claim 1, wherein the signal acquisition system includes an analog-to-digital converter and a digital signal processor.

6. A method for sensing signals from a brain, comprising:
    engaging an electrode array with the brain, the electrode array including a plurality of cells;
    sampling signals at the respective cells;
    aggregating, using an intelligent multiplexer, the signals; and
    transmitting an aggregated signal to a signal acquisition circuit for processing.

7. The method of claim 6, further comprising:
    holding the signals at the respective cells.

8. The method of claim 6, further comprising:
    time-aligning the signals prior to aggregating the signals.

9. The method of claim 7, wherein time-aligning the signals comprises:
    injecting a snapshot signal to the cells, the snapshot signal configured to control timings of sampling the signals at the respective cells.

* * * * *